US007871768B2

(12) United States Patent
Scherer et al.

(10) Patent No.: US 7,871,768 B2
(45) Date of Patent: Jan. 18, 2011

(54) LAFORA'S DISEASE GENE

(75) Inventors: Stephen W. Scherer, Toronto (CA);
Berge A Minassian, Toronto (CA)

(73) Assignee: The Hospital for Sick Children,
Toronto, Ontario (CA)

( * ) Notice: Subject to any disclaimer, the term of this patent is extended or adjusted under 35 U.S.C. 154(b) by 282 days.

(21) Appl. No.: 10/567,074

(22) PCT Filed: Jul. 30, 2004

(86) PCT No.: PCT/CA2004/001449

§ 371 (c)(1),
(2), (4) Date: Jun. 26, 2006

(87) PCT Pub. No.: WO2005/012526

PCT Pub. Date: Feb. 10, 2005

(65) Prior Publication Data

US 2007/0184442 A1 Aug. 9, 2007

Related U.S. Application Data

(60) Provisional application No. 60/491,968, filed on Aug. 4, 2003.

(51) Int. Cl.
C07H 21/04 (2006.01)
C12Q 1/68 (2006.01)
(52) U.S. Cl. ........................ 435/6; 435/91.1; 435/91.2; 536/23.1; 536/24.3
(58) Field of Classification Search ....................... None
See application file for complete search history.

(56) References Cited

U.S. PATENT DOCUMENTS

| 6,825,328 | B1 | 11/2004 | Scherer et al. | |
|---|---|---|---|---|
| 7,550,571 | B2 | 6/2009 | Delgado-Escueta et al. | |
| 2003/0092019 | A1* | 5/2003 | Meyer et al. .................. | 435/6 |
| 2004/0241740 | A1 | 12/2004 | Scherer et al. | |
| 2010/0009346 | A1 | 1/2010 | Scherer et al. | |

FOREIGN PATENT DOCUMENTS

| EP | 0705842 A2 | | 4/1996 |
|---|---|---|---|
| WO | WO 00/05405 A2 | | 2/2000 |
| WO | WO 00/05405 A3 | | 2/2000 |
| WO | WO2004038003 | * | 5/2004 |
| WO | WO 2005/012526 A1 | | 2/2005 |

OTHER PUBLICATIONS

Ianzano et al. Human Mutation Database in Brief #847, 2008.*
http://projects.tcag.ca/Iafora, Aug. 22, 2008.*
Lohi et al. (Neurology, vol. 68, pp. 996-1001, 2007).*
Chan et al. (J. Med. Genet. vol. 40, pp. 671-675, 2003).*
Chan et al. (Nature Genetics, vol. 35, No. 2, pp. 125-127, Sep. 2003).*
Singh et al. (J. Med Genetics, vol. 43, e48, 2006).*
Lucentini (The Scientist; 2004, vol. 24, p. 20).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Chan et al. (Nature Genetics, vol. 35, No. 2, pp. 125-127, Oct. 2003).*
Denu, J., et al., "Form and Function in Protein Dephosphorylation," *Cell*, vol. 87, pp. 361-364, Nov. 1, 1996.
Roes, et al., "Mouse Anti-Mouse IgD Monoclonal Antibodies Generated in IgD-Deficient Mice," Journal of Immunological Methods, pp. 231-237, 1995.
GenBank, Accession AJ130763, GI 3980308, Dec. 16, 1998.
deJong, P.J. "Preparation of PAC Libraries, Final Technical Report," Report No. DE-FG02-94ER61883—1, 7 pages plus cover sheet (Dec. 1997).
U.S. Office Action dated May 2, 2007 for U.S. Appl. No. 10/886,033.
U.S. Office Action dated Dec. 10, 2007 for U.S. Appl. No. 10/886,033.
U.S. Office Action dated May 23, 2008 for U.S. Appl. No. 10/886,033.
U.S. Office Action dated Nov. 28, 2008 for U.S. Appl. No. 10/886,033.
U.S. Office Action dated Dec. 24, 2002 for U.S. Appl. No. 09/744,072.
U.S. Office Action dated Oct. 22, 2003 for U.S. Appl. No. 09/744,072.
U.S. Office Action dated Mar. 18, 2010 for U.S. Appl. No. 11/979,262.
Canadian Office Action dated Apr. 22, 2010 for Canadian Application No. 2,338,250.
Wojcik, S.F., et al., "Cloning of Bovine Parathyroid Hormone-Related Protein (PTHrP) cDNA and Expression of PTHrP mRNA in the Bovine Mammary Gland," *J. Mol. Endocrinol.*, 20:271-280 (1998).
Serratosa, J.M., et al., "A Novel Protein Tyrosine Phosphatase Gene is Mutated in Progressive Myoclonus Epilepsy of the Lafora Type (EPM2)," *Human Molecular Genetics* 8(2):345-352 (1999).
Sainz, J., et al., "Lafora Progressive Myoclonus Epilepsy: Narrowing the Chromosome 6q24 Locus by Recombinations and Homozygosities," *Am. J. Hum. Genet.*, 61:1205-1209 (1997).
Lehesjoki, Anna-Elina, "Molecular Background of Progressive Myoclonus Epilepsy," *The EMBO Journal* 22(14):3473-3478 (2003).
Chan, E.M., et al., "Mutations in NHLRC1 Cause Progressive Myoclonus Epilepsy," *Nature Genetics* 35(2):125-127 (2003).
Minassian, B.A., et al., "Mutations in a Gene Encoding a Novel Protein Tyrosine Phosphatase Cause Progressive Myoclonus Epilepsy," *Nature Genetics* 20:171-174 (1998).
Chan, E.M., et al., "Genetic Mapping of a New Lafora Progressive Myoclonus Epilepsy Locus (EPM2B) on 6p22," *J. Med. Genet.*, 40:671-675 (2003).
Minassian, B.A., et al., "Progress Towards the Positional Cloning of a Gene for Lafora's Disease," *Neurology* 48:A428 (1997).
Database Sequence, Genbank Accession No. AK045746, 2006.
Database Sequence, Genbank Accession No. AL589723, 2007.
Database Sequence, Genbank Accession No. CAE62664, 2003.
Database Sequence, Genbank Accession No. AL023806, 2007.

(Continued)

Primary Examiner—Jeanine A Goldberg
(74) Attorney, Agent, or Firm—Hamilton, Brook, Smith & Reynolds, P.C.

(57) ABSTRACT

A novel gene (EPM2B) that is mutated in humans and dogs with Lafora's disease is described.

8 Claims, 15 Drawing Sheets

OTHER PUBLICATIONS

Cavanagh, J.B., "Corpora-amylacea and the Family of Polyglucosan Diseases," *Brain Research Reviews* 29: 265-295 (1999).

Freemont, Paul S., "Ubiquitination: RING for Destruction?" *Current Biology* 10: R84-R87 (2000).

Fridell, Robert A., et al., "Identification of a Novel Human Zinc Finger Protein that Specifically Interacts with the Activation Domain of Lentiviral Tat Proteins," *Virology* 209: 347-357 (1995).

Ganesh, Subramaniam, et al., "Targeted Disruption of the *Epm2a* Gene Causes Formation of Lafora Inclusion Bodies, Neurodegeneration, Ataxia, Myoclonus Epilepsy and Impaired Behavioral Response in Mice," *Human Molecular Genetics* 11(11): 1251-1262 (2002).

Ganesh, Subramaniam, et al., "Alternative Splicing Modulates Subcellular Localization of Laforin," *Biochemical and Biophysical Research Communications* 291: 1134-1137 (2002).

Ganesh, Subramaniam, et al., "Laforin, Defective in the Progressive Myoclonus Epilepsy of Lafora Type, is a Dual-Specificity Phosphatase Associated with Polyribosomes," *Human Molecular Genetics* 9(15): 2251-2261 (2000).

Hatakeyama, Shigetsugu, and Nakayama, Kei-ichi I., "U-box Proteins as a New Family of Ubiquitin Ligases," *Biochemical and Biophysical Research Communications* 302: 635-645 (2003).

Ianzano, Leonarda, et al., "Identification of a Novel Protein Interacting with Laforin, the *EPM2A* Progressive Myoclonus Epilepsy Gene Product," *Genomics* 81: 579-587 (2003).

Jackson, Peter K., et al., "The Lore of the RINGs: Substrate Recognition and Catalysis by Ubiquitin Ligases," *Cell Biology* 10: 429-439 (2000).

Lalioti, Maria D., et al., "Dodecamer Repeat Expansion in Cystatin B Gene in Progressive Myoclonus Epilepsy," *Nature* 386: 847-851 (1997).

Licht, Barbara G., et al., "Clinical Presentations of Naturally Occurring Canine Seizures: Similarities to Human Seizures," *Epilepsy & Behavior* 3: 460-470 (2002).

Lossos, Alexander, M.D., et al., "Adult Polyglucosan Body Disease in Ashkenazi Jewish Patients Carrying the TYR$^{329}$Ser Mutation in the Glycogen-Branching Enzyme Gene," *Annals of Neurology*, 44(6): 867-872 (1998).

Minassian, B.A., M.D., et al. "Mutation Spectrum and Predicted Function of Laforin in Lafora's Progressive Myoclonus Epilepsy," *Neurology* 55: 341-346 (2000).

Minassian, Berge A., et al., "Laforin is a Cell Membrane and Endoplasmic Reticulum-Associated Protein Tyrosine Phosphatase," *Annals of Neurology* 49(2): 271-275 (2001).

Minassian, Berge A., M.D., et al., "Genetic Locus Heterogeneity in Lafora's Progressive Myoclonus Epilepsy," *Annals of Neurology* 5(2): 262-265 (1999).

Schoeman, Tanya, et al., "Polyglucosan Storage Disease in a Dog Resembling Lafora's Disease," *J. Vet. Intern. Med.* 16: 201-207 (2002).

Thon, Vicki J., et al., "Isolation of Human Glycogen Branching Enzyme cDNAs by Screening Complementation in Yeast," *The Journal of Biological Chemistry*, 268(10): 7509-7513 (1993).

Weinhaeusel, Andreas, et al., "DNA Deamination Enables Direct PCR Amplification of the Cystatin B (CSTB) Gene-Associated Dodecamer Repeat Expansion in Myoclonus Epilepsy Type Unverricht-Lundborg," *Human Mutation* 22: 404-408 (2003).

Japanese Office Action dated May 26, 2010 for Japanese Patent Application No. 2006-522189.

Collins, F., "Generation and initial analysis of more than 15,000 full-length human and mouse cDNA sequences", *PNAS*, vol. 99(26), pp. 16899-16903 (Oct. 2002).

* cited by examiner

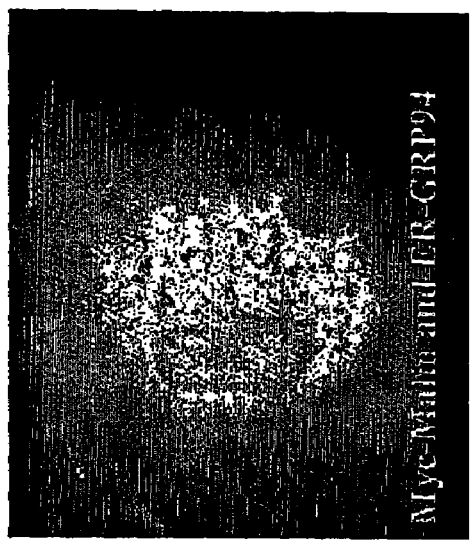
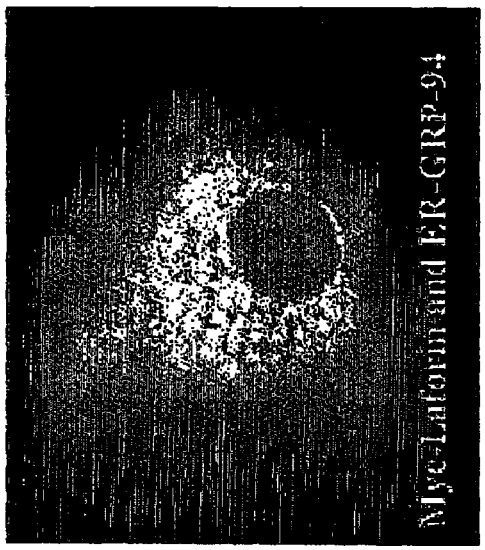
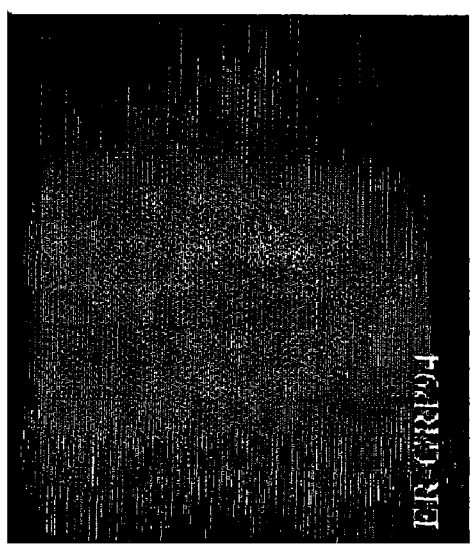
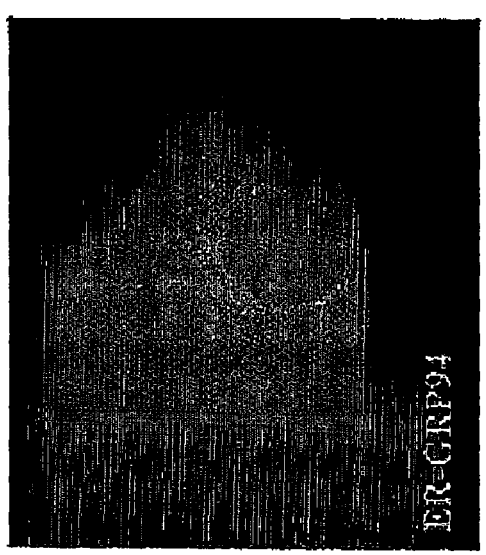
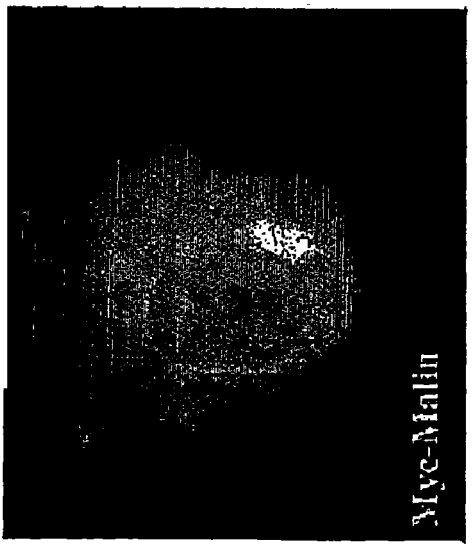
Fig 5a
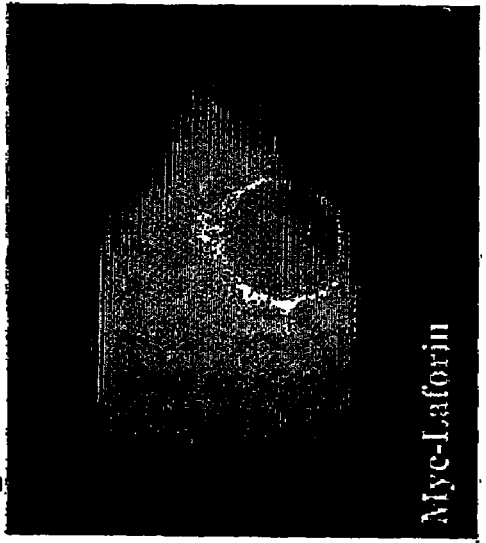
Fig 5b

Fig 6A

```
   1 atggcggccg aagcctcgga gagcgggcca gcgctgcatg agctcatgcg cgaggcggag
  61 atcagcctgc tcgagtgcaa ggtgtgcttt gagaagtttg ccaccggca gcagcggcgc
 121 ccgcgcaacc tgtcctgcgg ccacgtggtc tgcctggct gcgtggccgc cctggcgcac
 181 ccgcgcactc tggccctcga gtgcccattc tgcaggcgag cttgccgggg ctgcgacacc
 241 agcgactgcc tgccggtgct gcacctcata gagctcctgg gctcagcgct tcgccagtcc
 301 ccggccgccc atcgcgccgc cccagcgcc ccggagccc tcacctgcca ccacccttc
 361 ggcggctggg ggaccctggt caaccccacc ggactggcgc tttgtcccaa gacggggcgt
 421 gtcgtggtgg tgcacgacgg caggaggcgt gtcaagattt ttgactcagg gggaggatgc
 481 gcgcatcagt ttggagagaa gggggacgct gcccaagaca ttaggtaccc tgtggatgtc
 541 accatcacca acgactgcca tgtggttgtc actgacgccg gcgatcgctc catcaaagtg
 601 tttgatttt ttggccagat caagcttgtc attggaggcc aattctcctt accttggggt
 661 gtggagacca ccctcagaa tgggattgtg gtaactgatg cggaggcagg gtccctgcac
 721 ctcctggacg tcgacttcgc ggaaggggtc cttcggagaa ctgaaaggtt gcaagctcat
 781 ctgtgcaatc cccgagggt ggcagtgtct tggctcaccg gggccattgc ggtcctggag
 841 cacccctgg ccctggggac tggggtttgc agcaccaggg tgaaagtgtt tagctcaagt
 901 atgcagcttg tcggccaagt ggatacctt gggctgagcc tctactttcc ctccaaaata
 961 actgcctccg ctgcgacctt tgatcaccag ggaaatgtga ttgttgcaga tacatctggt
1021 ccagctatcc tttgcttagg aaaacctgag gagtttccag taccgaagcc catggtcact
1081 catggtcttt cgcatcctgt ggctcttacc ttcaccaagg agaattctct tcttgtgctg
1141 gacacagcat ctcattctat aaaagtctat aaagttgact gggggtgatg ggctggggtg
1201 ggtccctgga atcagaagca ctagtgctgc cattaatgaa ttgtttaacc ctggataagt
1261 cacttaaact catctatcca ggcagggata attaaaacca tctggcagac ttacaaagct
1321 tgggacagtt attggagatt aatctaccat ttattgaatg catactctgt gcaaggaaat
1381 ttgcaaatat tagcttattt aatctgtact atccagtgag gtaatttctt ccccccaag
1441 atagagtcaa gctctgtcac ccaggctgga gtgcagaagc atgatcacag ctcactacag
```

SEQ ID NO: 1

Fig 6A (cont'd)

```
1501 tttcaacgtc ccccgctcag gtggtccttc cacctcagcc tcccaagtag ctgggaccac
1561 aagtgtgcat taccacactc agctaatttt tgtattttgg cagagatggg gtttcaccat
1621 gttgcccagg ctggtctcaa actcctgagt tcaagcaatc caccttcctc ggcctcccaa
1681 agtactagga gtacaggcat agccacttgc tcagccataa ttttattat taatctcatt
1741 gtacaagtga aaaactgag acccagagag cttaagtgac ttcctcgagg tcatagttac
1801 ttactgcctt agtcccaatt tgaattcaat tctgattcca aataagttgc gcttaaataa
1861 gacaacagat gtgggaaaaa tatgtgaatg tgtagtgttg ctatgtgtac tgtctttaca
1921 agtagctaat tattttagca caaagatgtg caaagaaagg agactttatg gagagttcag
1981 gagaaaaagg attttgtggt ggccatcact ttcattcaat ttgcgactgc tctgatggca
2041 cattagatga agttactgtt gatcctgagt tacgtgaata agaaaaacaa ttgaactgct
2101 tattaaaaaa gtaaacatgt
```

Fig 6B

EPM2B protein sequence

MAAEASESGPALHELMREAEISLLECKVCFEKFGHRQQRRPRNLSCGHVV
CLACVAALAHPRTLALECPFCRRACRGCDTSDCLPVLHLIELLGSALRQS
PAAHRAAPSAPGALTCHHTFGGWGTLVNPTGLALCPKTGRVVVVHDGRRR
VKIFDSGGGCAHQFGEKGDAAQDIRYPVDVTITNDCHVVVTDAGDRSIKV
FDFPGQIKLVIGGQFSLPWGVETTPQNGIVVTDAEAGSLHLLDVDFAEGV
LRRTERLQAHLCNPRGVAVSWLTGAIAVLEHPLALGTGVCSTRVKVFSSS
MQLVGQVDTFGLSLYFPSKITASAVTFDHQGNVIVADTSGPAILCLGKPE
EFPVPKPMVTHGLSHPVALTFTKENSLLVLDTASHSIKVYKVDWG.

SEQ ID NO:2

Fig 7A

Promoter (5') sequence:

```
   1 CCCCAAGGCC CCCCCGGCCC CCAGGCAACC CCAGGCCCCC AGGCAACCCA
  51 AGGCCCCCCG GCCCCAAGCC CCCCAGGTTC CCGGCCCCAA GAACCAAGCC
 101 CCCCGGCCCC CCGCCCCCAG CACCCAGCAC CAAGCCCCCG CCCCCCGCCC
 151 CAAGCACCCA GCCCCAGCAC CCAGCCCCCG CCCCAGCCCC AGCCCCAGCA
 201 CCCAGCCCCC GCCCCAGCAC CCAGCCCCAG CACCCAGCCC CCGCCCCAGC
 251 CCCAGCCCCC GTCCCCCCCC CCAGCACCCA GCCCCAGCCC CAGCAGCAGC
 301 ACCCAGCAGG GGACTGCAAA GCGTAGGCTA CCCCAGGTGG AACACCGTGT
 351 TCTAGTTTTG CTTTGCCGTT TGCAGCCTGG GCGATCGGGG GCCACCGCTC
 401 GAGCCTGTTT CCCGTCGCGG AAAGCGGAGC CGCCCCGCCC CGCCCCCCGC
 451 CTGCCTGAAG GTCACGGGCC TGGGCCTGCG GCGCGCGGTG CGGCCCGCGA
 501 GCGTCCGCTC CCGCGCCCTC CGCAGTCAGC GCCCGCCCGC CCGCCGGGGG
 551 ACCGCAGGCC GCGGCCGAGA GGCTGCGCGC TGCGCCCGCG ACGTCAGGCC
 601 CCGCCCCGCC CCGCCCCGCC CCGTGACCGG CCCCGGCCCC GGCCCCGGCC
 651 CCGGCCCCGG ACCGAGCGGC GCCCGCGGGA GCGGCGGCGG CCGCGCG
```

Coding sequence:

```
        ATG
 701 GGGGCCGAAG CGGCGGGGAG CGGGCGGGCG CTGCGGGAGC TGGTGCGCGA
 751 GGCCGAGGTC AGCTTGCTCG AGTGCAAGGT GTGCTTCGAG AGGTTCGGCC
 801 ACCGCCAGCA GCGGCGCCCG CGCAACCTGC CCTGCGGCCA CGTGGTGTGC
 851 CTGGCCTGCG TGGCGGCCCT GGCGCACCCG CGGACGCTGG CCCTGGAGTG
 901 CCCCTTCTGC CGCCGGGCCT GCCGCGGCTG CGACACCAGC GACTGCCTGC
 951 CGGTGCTTCA CCTCCTGGAG CTCCTGGGCT CGGCGCTGCG CCCAGCCCCC
1001 GCCGCCCCCC GCGCCGCCCC CCGCGCCGCC CCCTGCGCCC CGGGCGCCCT
1051 CGCCTGCCAT CACGCGTTCG GAGGCTGGGG GACCCTGGTC AACCCCACGG
1101 GGCTGGCGCT GTGCCCCAAG ACCGGGCGGG TCGTGGTGGT GCACGACGGC
1151 AGGAGGCGGG TCAAGATCTT TGACTCCGGG GGAGGATGCG CCCATCAGTT
1201 TGGAGAGAAG GGGGAGGCTG CCCAGGACAT TAGGTACCCC CTGGACGTCG
1251 CCGTCACCAA CGACTGCCAC GTGGTTGTCA CCGACGCCGG CGACCGCTCC
1301 ATCAAAGTGT TTGATTTCTT TGGCCAGATC AAGCTCGTCA TTGGAGACCA
1351 GTTTTCCTTA CCTTGGGGCG TGGAGACCAC CCCTCAGAAT GGGGTCGTGG
1401 TAACTGACGC CGAGGCAGGG TCGCTGCACC TGCTGGAAGT CGACTTTGCA
1451 GAAGGAGCCC TCCAGAGGAC TGAAAAGCTG CAAGGTCATC TGTGCAACCC
1501 GCGAGGGGTG GCCGTGTCCT GGCTCACTGG GGCCATTGCG GTCCTGGAGC
1551 ACCCTCCGGG GCTGGGGGCT GGGGCGGGCA GCACCGCCGT GAAGGTGTTC
1601 AGCCCAACTA TGCAGCTGAT CGGCCAGGTG GATACCTTTG GGCTCAGCCT
1651 CTTTTTCCCC TCTAGAATAA CCGCCTCCGC CGTGACCTTT GATCACCAGG
1701 GGAATGTGAT TGTTGCAGAT ACTTCTAGTC AGGCCGTCCT ATGCTTGGGA
1751 CAGCCTGAGG AATTTCCAGT CCTGAAGCCC ATCATCACCC ATGGTCTTTC
1801 CCATCCTGTG GCACTGACCT TCACCAAGGA GAATTCTCTT CTTGTGCTGG
1851 ACAGTGCAGC CCATTCCGTA AAAGTCTACA AGGCTGACTG GGGGTAA
```

SEQ ID NO: 3

Fig 7A (cont'd)

3' UTR:

```
         TGG
1901 GGTGTGGTGG GGGTCCTGGA ACTGCCACTA ATCCAGTTTA ACCCTGGATG
1951 AATTAATCCC ATCTCTCGAA CGGGGATCAT TATAACTGCC TGACAGACTT
2001 ATAAAGGTTG AAGGTAATTA TTAAAGAATA ATAATGAAGT CTACCGTTTA
2051 TTGAGTTATG TGCTCCCTGT GCTAGGAAAC TTTGCAAATA TTAGCTCAGC
2101 GTGTCCTTAC AGTGGTACCC AGGGAGGTAA TGCCCATCAT TAATCCCATT
2151 TTAGAGATGA GAAAACTGAG ACCCGAGGGT TAAGTGATT  CTCTGAAGGT
2201 CATGTTTACT TACTGTGACA GTCACAATGG GAACTCTATT CTGACTCCCC
2251 AATCCCTTGC TCCTAAGTAG GATAACAGAT GTGAGAAAAC GACAGCATGT
2301 GTCTATATGT TGTTACTGTG TGTACTCTCT TTACAGGTAG CTATTTCTCT
2351 TGGTTGGACG TGCAGAGAAA GGAGACTTTC TAGAGAGTTC AAGAGGAAAA
2401 AGGGTAGTGT GATGAGCATG GACGTGAGTG TCATTGAACT TGCTGGTTCT
2451 TTGATGTCAC AGTAGGTAGA ATGACTGTGG ATCCTTCAAC TGCCCTTGGG
2501 AAAGGTAAAC ATGTCTGTTG GGACCTGGAT GTCCTCCATC ATAGGAACCC
2551 AGGAAATACT AGTTGGTTGC TGCAGAAAGG CTTGTGTGGA CATAAGTTCA
2601 AAACTACTGC CGACCACCGT ACATTCACAC ACCTCCAGTG GGAGATGGCT
2651 GGAAGACAGT CCTGTGACAG GTCTGCATTC ATAGAACAAG ANGCCGCCAC
2701 CGTTGGTTCA CGGCAGAATG AGTTTGCCTG CCTCTTCATA ATCTGTGNCN
2751 ACCCGAAACC CTTTTGTGAT AGAGTTTTTC TCTGTGCCAT TTNAATTTGT
2801 CCCATTGCAC ACACTGTTTT CCCCTAACCA GCTCCCTTGA TGCTNAGCTA
2851 GCATTTAGGC CACTGGTAAA CCCCTGTATA CTTCTTGAGT TGAAGTTAAG
2901 CTTTGACCCA GATAANGNCT GCTTTAATAC NTGCAGTCGA NTGGACCGAA
2951 TAAGGGGGAA ATTTCAGGTG AGGTGGCCGG GTTCTTTATN AACCGGTTTT
3001 GGTTTGTA
```

Fig 7B

```
Met Gly Ala Glu Ala Ala Gly Ser Gly Arg Ala Leu Arg Glu Leu Val
1               5                   10                  15

Arg Glu Ala Glu Val Ser Leu Leu Glu Cys Lys Val Cys Phe Glu Arg
            20                  25                  30

Phe Gly His Arg Gln Gln Arg Arg Pro Arg Asn Leu Pro Cys Gly His
        35                  40                  45

Val Val Cys Leu Ala Cys Val Ala Ala Leu Ala His Pro Arg Thr Leu
    50                  55                  60

Ala Leu Glu Cys Pro Phe Cys Arg Arg Ala Cys Arg Gly Cys Asp Thr
65              70                  75                  80

Ser Asp Cys Leu Pro Val Leu His Leu Leu Glu Leu Leu Gly Ser Ala
                85                  90                  95

Leu Arg Pro Ala Pro Ala Ala Pro Arg Ala Ala Pro Arg Ala Ala Pro
            100                 105                 110

Cys Ala Pro Gly Ala Leu Ala Cys His His Ala Phe Gly Gly Trp Gly
            115                 120                 125

Thr Leu Val Asn Pro Thr Gly Leu Ala Leu Cys Pro Lys Thr Gly Arg
    130                 135                 140

Val Val Val Val His Asp Gly Arg Arg Arg Val Lys Ile Phe Asp Ser
145                 150                 155                 160

Gly Gly Gly Cys Ala His Gln Phe Gly Glu Lys Gly Glu Ala Ala Gln
            165                 170                 175

Asp Ile Arg Tyr Pro Leu Asp Val Ala Val Thr Asn Asp Cys His Val
            180                 185                 190

Val Val Thr Asp Ala Gly Asp Arg Ser Ile Lys Val Phe Asp Phe Phe
        195                 200                 205

Gly Gln Ile Lys Leu Val Ile Gly Asp Gln Phe Ser Leu Pro Trp Gly
        210                 215                 220
```

SEQ ID NO: 4

Fig 7B (cont'd)

```
Val Glu Thr Thr Pro Gln Asn Gly Val Val Thr Asp Ala Glu Ala
225                 230             235             240

Gly Ser Leu His Leu Leu Glu Val Asp Phe Ala Glu Gly Ala Leu Gln
            245             250             255

Arg Thr Glu Lys Leu Gln Gly His Leu Cys Asn Pro Arg Gly Val Ala
            260             265             270

Val Ser Trp Leu Thr Gly Ala Ile Ala Val Leu Glu His Pro Pro Gly
        275             280             285

Leu Gly Ala Gly Ala Gly Ser Thr Ala Val Lys Val Phe Ser Pro Thr
    290             295             300

Met Gln Leu Ile Gly Gln Val Asp Thr Phe Gly Leu Ser Leu Phe Phe
305             310             315             320

Pro Ser Arg Ile Thr Ala Ser Ala Val Thr Phe Asp His Gln Gly Asn
            325             330             335

Val Ile Val Ala Asp Thr Ser Ser Gln Ala Val Leu Cys Leu Gly Gln
            340             345             350

Pro Glu Glu Phe Pro Val Leu Lys Pro Ile Ile Thr His Gly Leu Ser
        355             360             365

His Pro Val Ala Leu Thr Phe Thr Lys Glu Asn Ser Leu Leu Val Leu
        370             375             380

Asp Ser Ala Ala His Ser Val Lys Val Tyr Lys Ala Asp Trp Gly
385             390             395
```

LAFORA'S DISEASE GENE

RELATED APPLICATIONS

This application is the U.S. National Stage of International Application No. PCT/CA2004/001449, filed 30 Jul. 2004, published in English, and claims priority under 35 U.S.C. §119 or 365 to U.S. Provisional Application No. 60/491,968, filed 4 Aug. 2003.

FIELD OF THE INVENTION

The invention relates to a novel gene, EPM2B, that is involved in Lafora's disease; the protein, malin, encoded by the gene; and methods of diagnosing and treating Lafora's disease.

BACKGROUND OF THE INVENTION

Lafora's disease (LD, OMIM 254780) is the most common and severe form of adolescent-onset progressive epilepsy. Increasing seizures are paralleled with an insidious cognitive decline towards dementia, and death usually within 10 years of onset (1,2). At the cellular level, LD is characterized by an endoplasmic reticulum (ER)-associated accumulation (3) of starch-like glucose polymers (4) called polyglucosans (or Lafora bodies). Inheritance is autosomal recessive with genetic heterogeneity but the clinical presentation is homogeneous (5). The inventors previously discovered that mutations in the EPM2A gene on chromosome 6q24 encoding a dual-specificity phosphatase (named Laforin) with a carbohydrate binding domain, cause LD (6, 7 and WO 00/05405).

There is a need in the art to identify other genes involved in Lafora's disease to assist in the diagnosis and treatment of Lafora's disease.

SUMMARY OF THE INVENTION

The present inventors positionally cloned a novel gene, EPM2B, on chromosome 6p22.3. It encodes a protein with a putative RING-finger domain and 6 NHL-motifs, which are features of complexes designed for ubiquitin-mediated regulation of specific substrates (8,9) and protein-protein interactions (10-13), respectively. Twenty-one distinct DNA sequence variations in EPM2B predicted to cause deleterious effects on the protein product, named malin, were found to co-segregate with LD in 39 families. Both laforin and malin localize to the ER suggesting they operate in a related pathway protecting against neuronal polyglucosan accumulation and epilepsy. The inventors have also isolated and sequenced the canine version of EPM2B and have shown a mutation in EPM2B in dogs with LD.

Accordingly, the present invention provides an isolated nucleic acid molecule that is associated with Lafora's disease and having the sequence shown in SEQ ID NO:1 (FIG. 6A) (human EPM2B). The present invention also provides an isolated nucleic acid molecule that is associated with Lafora's disease and having a sequence shown in SEQ ID NO:3 (FIG. 7A) (canine EPM2B).

Preferably, the purified and isolated nucleic acid molecule comprises:

(a) a nucleic acid sequence as shown in SEQ ID NO:1 (FIG. 6A) and SEQ ID NO:3 (FIG. 7A), wherein T can also be U;

(b) a nucleic acid sequence complementary to (a);

(c) a nucleic acid sequence that has substantial sequence homology to a nucleic acid sequence of (a) or (b);

(d) a nucleic acid sequence that is an analog of a nucleic acid sequence of (a), (b) or (c); or (e) a nucleic acid sequence that hybridizes to a nucleic acid sequence of (a), (b), (c) or (d) under stringent hybridization conditions.

The present invention also includes an isolated protein containing a zinc finger of the RING type and 6 NHL-repeat domains which is associated with Lafora's disease. In a preferred embodiment of the invention, the protein has the amino acid sequence as shown in SEQ ID NO:2 (FIG. 6B) (human EPM2B). In another embodiment, the protein has the amino acid sequence shown in SEQ ID NO:4 (FIG. 7B) (canine EPM2B).

As shown in Table 1, the inventors have found 21 different mutations in the human EPM2B gene that are associated with Lafora's disease. Accordingly, the present invention provides a method of detecting Lafora's disease comprising detecting a mutation in the EPM2B gene in a sample from a mammal, preferably human. In a preferred embodiment, the mutation is one listed in Table 1.

The inventors have also discovered a mutation in the EPM2B gene in dogs with Lafora's disease. In particular, all affected dogs studied had a bi-allelic expansion of a dodecamer repeat, termed D, and having the sequence GCCGCCCCCCGC that starts at nucleotide number 1001 of canine EPM2B sequence shown in SEQ ID NO:3. Accordingly, the invention further provides a method of detecting Lafora's disease in a canid comprising detecting a repeat of the sequence GCCGCCCCCCGC (SEQ ID NO:5) which starts at nucleotide number 1001 in the canine sequence of EPM2B (SEQ ID NO:3).

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

Figure 1:
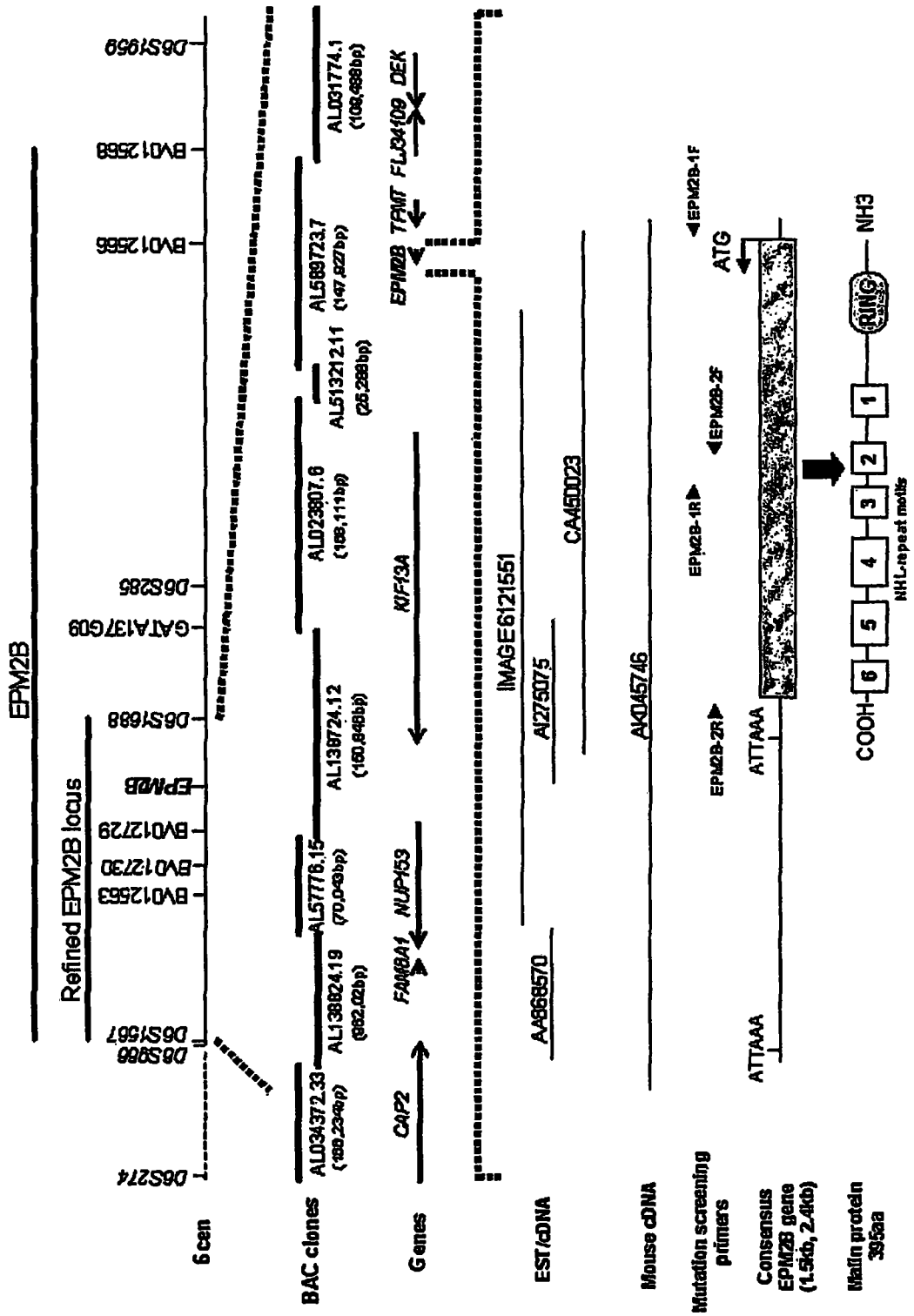
FIG. 1. The EPM2B region on 6p22.3. The previous 2.2 Mb critical interval was delimited by microsatellite markers D6S1567 and BV012568 (15). The BV012568 boundary was based on loss of homozygosity in LD individuals from an F-C family (LD6; see FIG. 2). The D6S1567 telomeric boundary was defined by a recombination occurring between BV012563 and D6S1567 in an unaffected sibling of a second consanguineous F-C family (15) (LD27). A break in the chain of homozygosity of markers in the LD38324 family allowed the centromeric boundary to be further re-defined to D6S1688 (FIG. 2) The region contains 7 previously annotated genes and the newly discovered EPM2B (FIG. 6A), which comprised of a single 1188 bp coding exon. Representative human and mouse cDNA sequences are shown, as are the putative ATG start and AATAAA polyadenylation signals. The ATG start follows an in-frame stop (at position −60) and the corresponding AUG is present at the beginning of the predicted ORF. The nucleotide sequence surrounding the start (CGCGCCAUGG) has the proposed features of the consensus sequence (GCCA/GCCAUGG) of an eukaryotic translation initiation site (29). EPM2B is predicted to encode a 42.3 kDa (395 aa) protein (malin) containing detectable zinc-binding RING-finger and 6 NHL-repeat domains (FIG.

6B). The RING and NHL acronyms arise from descriptions of the first proteins identified to carry them, namely, the Really interesting New Gene 1 in Homo sapiens (30) and the NCL-1 (11)/HT2A (10)/LIN-41 (13) genes, respectively. It should be noted that RING- and/or NHL-domains occur in a variety of proteins which can have one or both of cytoplasmic or nuclear localization (8,9,12,18). Malin is the only protein so far described having RING and NHL motifs only (there are other proteins with this combination but they also have other associated motifs such as RING-B-Box-coiled-coil domains). The site of a common C332T (P111L) polymorphism is shown by an askerisk (*) (see Table 1). Malin shares 79%, 80%, and 85% homology with the predicted rat (419 aa), mouse (401 aa) and dog (402 aa) proteins, respectively. The variable amino acids were primarily located in the carboxy- and amino-ends of the protein and not in the RING finger or NHL domains. The microsatellite markers beginning with BV- were generated in this study.

FIG. 2. Refinement of the EPM2B critical interval by haplotype analysis in LD families and mutations in the EPM2B gene. a, The centromeric boundary was narrowed to D6S1688 refining the critical region to 840 kb based on the loss of homozygosity in both probands in family LD38324. b, Sequence analysis of EPM2B identifies a homozygous 76T>A change in family LD6 (as well as in the LD7, LD27, and LD28 F-C families, Table 1). Affected individuals in family LD38324 were found to be homozygous for a dinucleotide deletion (1048-1049delGA) leading to frame-shift mutation in the fifth NHL domain.

Figure 3:
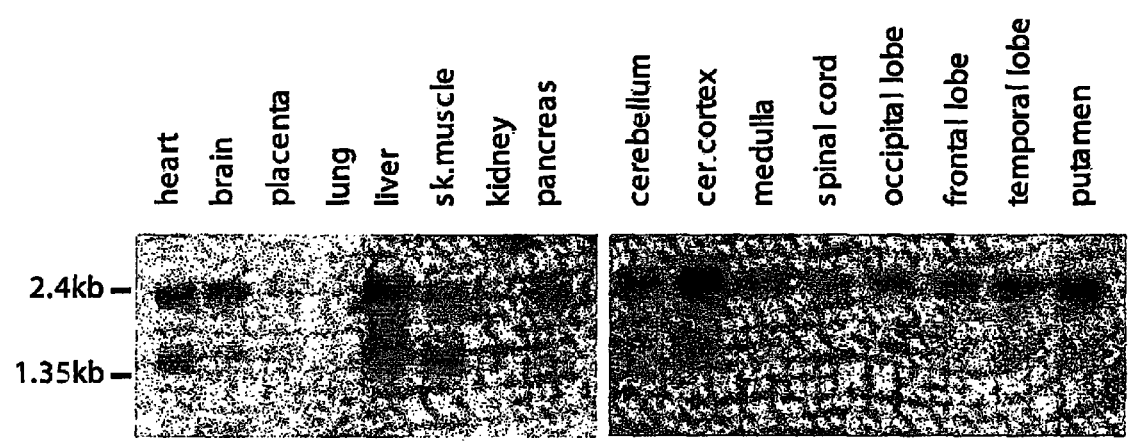

FIG. 3. RNA hybridization expression analysis of EPM2B in human tissues. a, A multiple tissue blot (Clontech) was hybridized with a 557 bp fragment of the coding region of EPM2B. Two transcripts 2.4 kb and 1.5 kb in size were identified in all tissues. b, The same sized transcripts were found in tissues from all regions of the brain tested.

Figure 4:
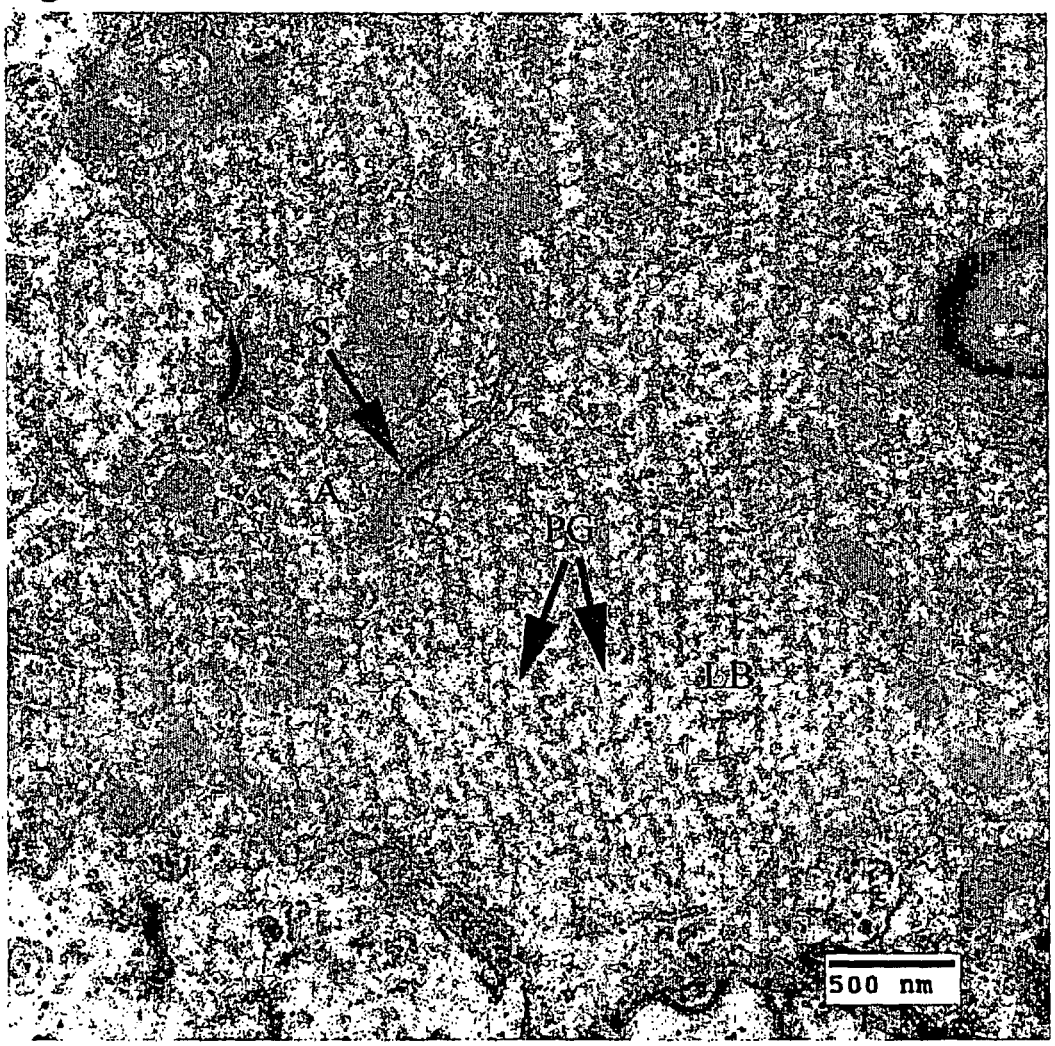

FIG. 4. Electron micrograph of brain biopsy material from patient LD32817 (EPM2B mutation 98T>C). A, axon (note the numerous normal neurotransmitter vesicles); S, synapse; LB, Lafora body (large rounded structure) composed of a dense accumulation of polyglucosan filaments (PG) completely occupying the dendrite. Bar equals 500 nm.

FIG. 5. Cellular localization of the malin and laforin proteins. a, Myc-tagged malin (construct pcDNA3mycEPM2B) forms a distinct reticular pattern around the nucleus, as well as within the nucleus. Co-staining with antibody against the GRP94 endoplasmic reticulum (ER)-specific marker reveals co-localization with malin. b, Co-localization of the cytoplasmic isoform of laforin (construct pcDNA3mycEPM2A (24)) with the ER-specific marker GRP94.

FIGS. 6A and B (SEQ ID NOS:1 and 2) provides the human nucleic acid and amino acid sequence of EPM2B.

FIGS. 7A and B (SEQ ID NOS:3 and 4) provides the canine nucleic acid and amino acid sequence for EPM2B.

Figure 8:
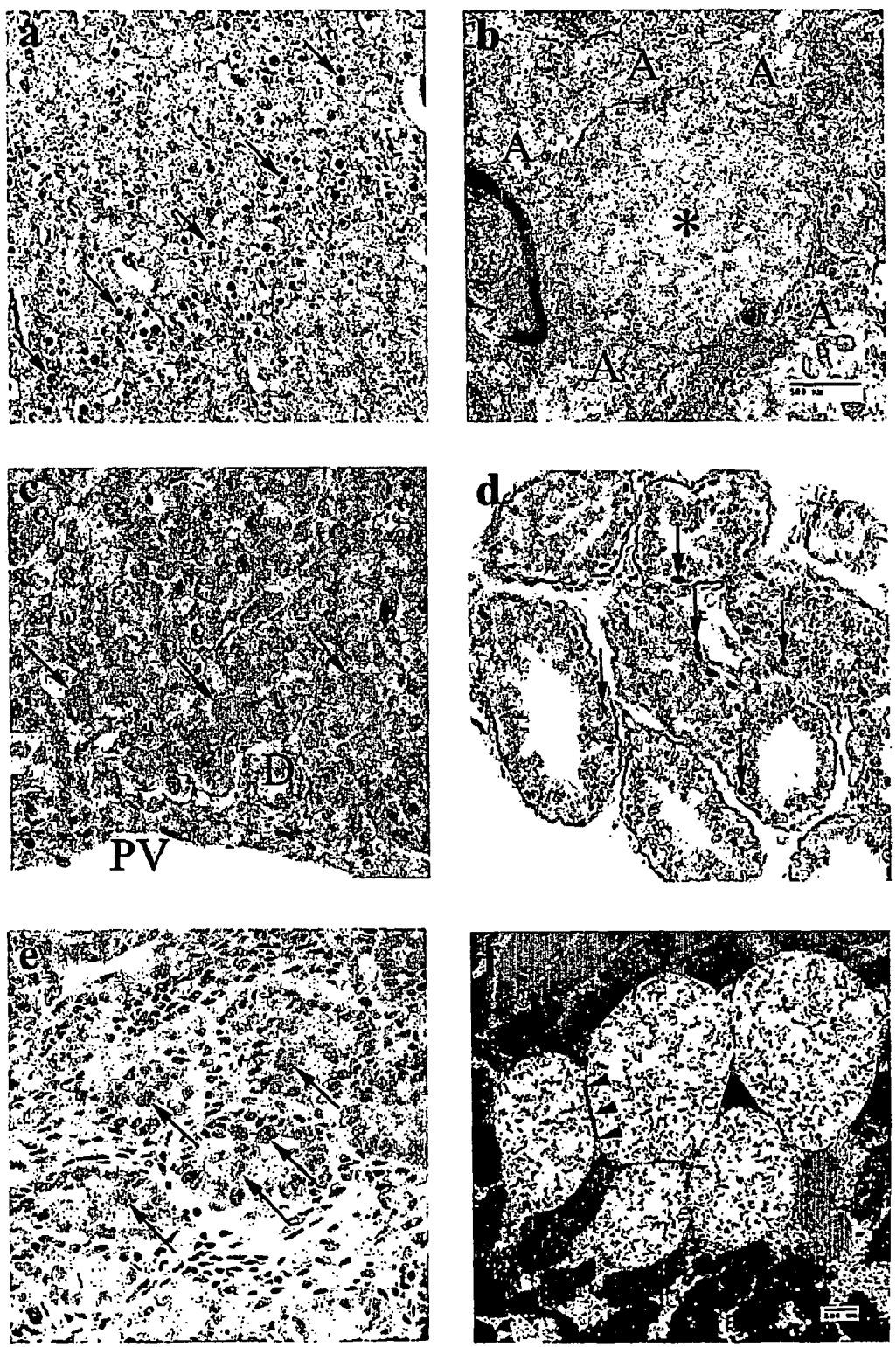

FIG. 8 shows the profuse starch-like polyglucosan accumulations (Lafora Bodies; LB) form in tissues of affected MWHD with characteristics and cellular distribution patterns identical to human LD (1,29,30). Affected MWHD tissues included nine muscle and two liver biopsies, as well as skin samples and four whole brains obtained at necropsy. Control tissues did not exhibit LB (seven age-matched animals including two normal MWHD and three non-LD epileptic dogs) and are not shown. Histochemical slides were stained with periodic acid-Schiff following diastase treatment, which allows specific detection of polyglucosans (1). Innumerable LB were present throughout the brain in affected MWHD, located, as in human LD (1), in neurons and not glia and in neuronal perikarya and dendrites and not axons: a, LB (arrows) in the molecular layer of cerebral cortex (×100 magnification); b, Example of a dendritic LB (asterisk); multiple axons (A) synapsing with this dendrite do not contain LB (bar=500 nm). c, In liver, LB (arrows) were only in gluconeogenic (periportal) hepatocytes, as in human (29); (PV, portal vein; D, portal ductule; ×300). d, e, In skin, LB (arrows) were in sweat glands, specifically, as in human (30), in myoepithelial cells surrounding apocrine sweat glands (d, ×100) and duct cells of merocrine sweat glands (e, foot pad skin tissue, ×250). f, In skeletal muscle, LB were within vacuoles surrounded by membranes (arrowheads), again as in human LD (29) (bar=500 nm).

Figure 9:
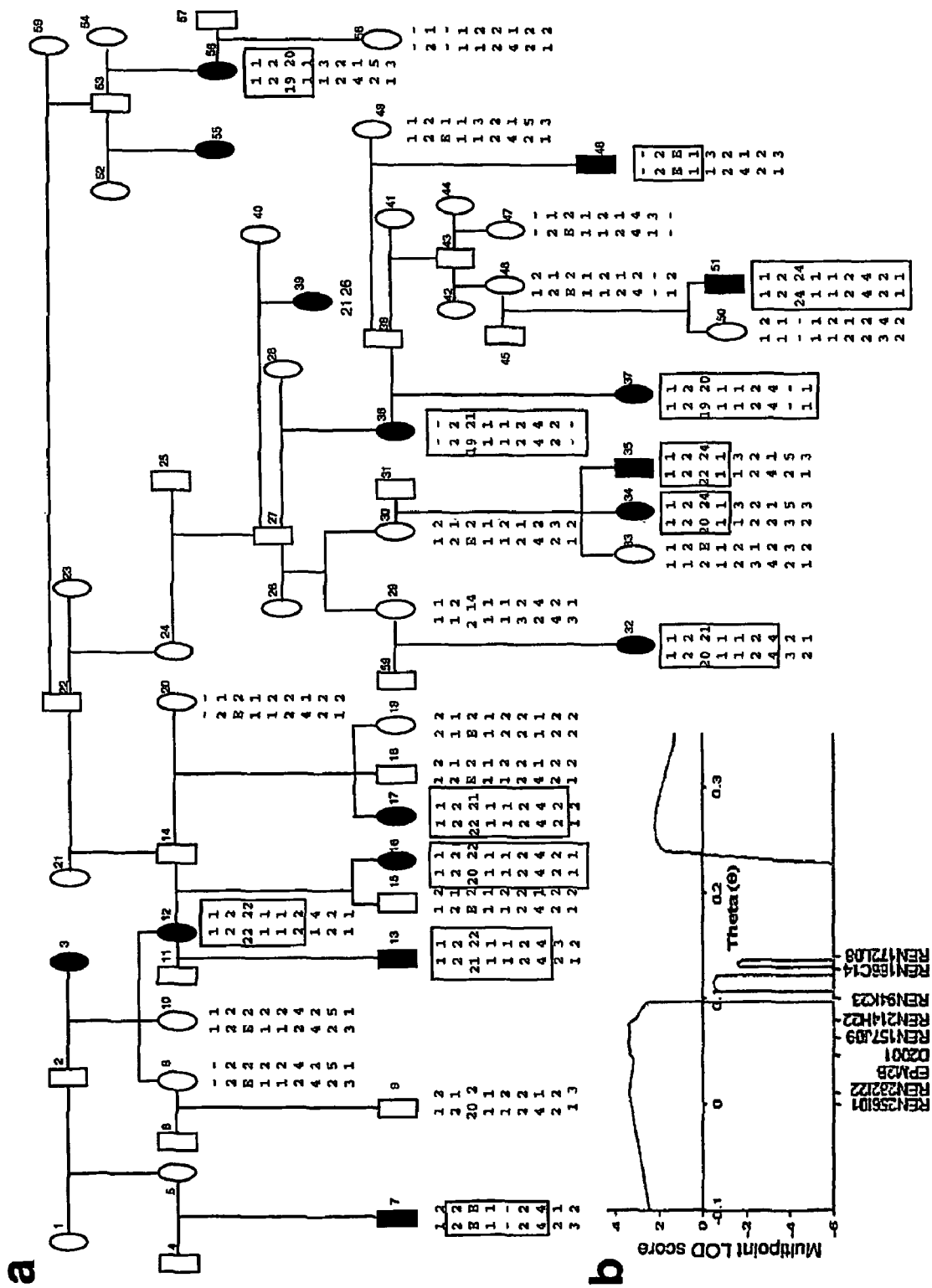

FIG. 9 shows MWHD LD links to the EPM2B gene, which contains an expansion mutation in affected dogs. a, Pedigree and haplotypes; numbers in black are genotypes, in descending order, at chromosome CFA35 microsatellites REN256101, REN282122, D02001, REN157J09, REN214H22, REN94K23, REN166C14, REN172L08; in red, the position of the EPM2B gene and the number of D repeats in its coding polymorphic dodecamer repeat; note: expansion mutations are meiotically unstable (e.g. see transmission of expansion from dog 29 to dog 32); E, expanded alleles with precise repeat number not determined; boxes, genotype homozygosities flanking the mutation. b, Multipoint LOD score analysis.

Figure 10:
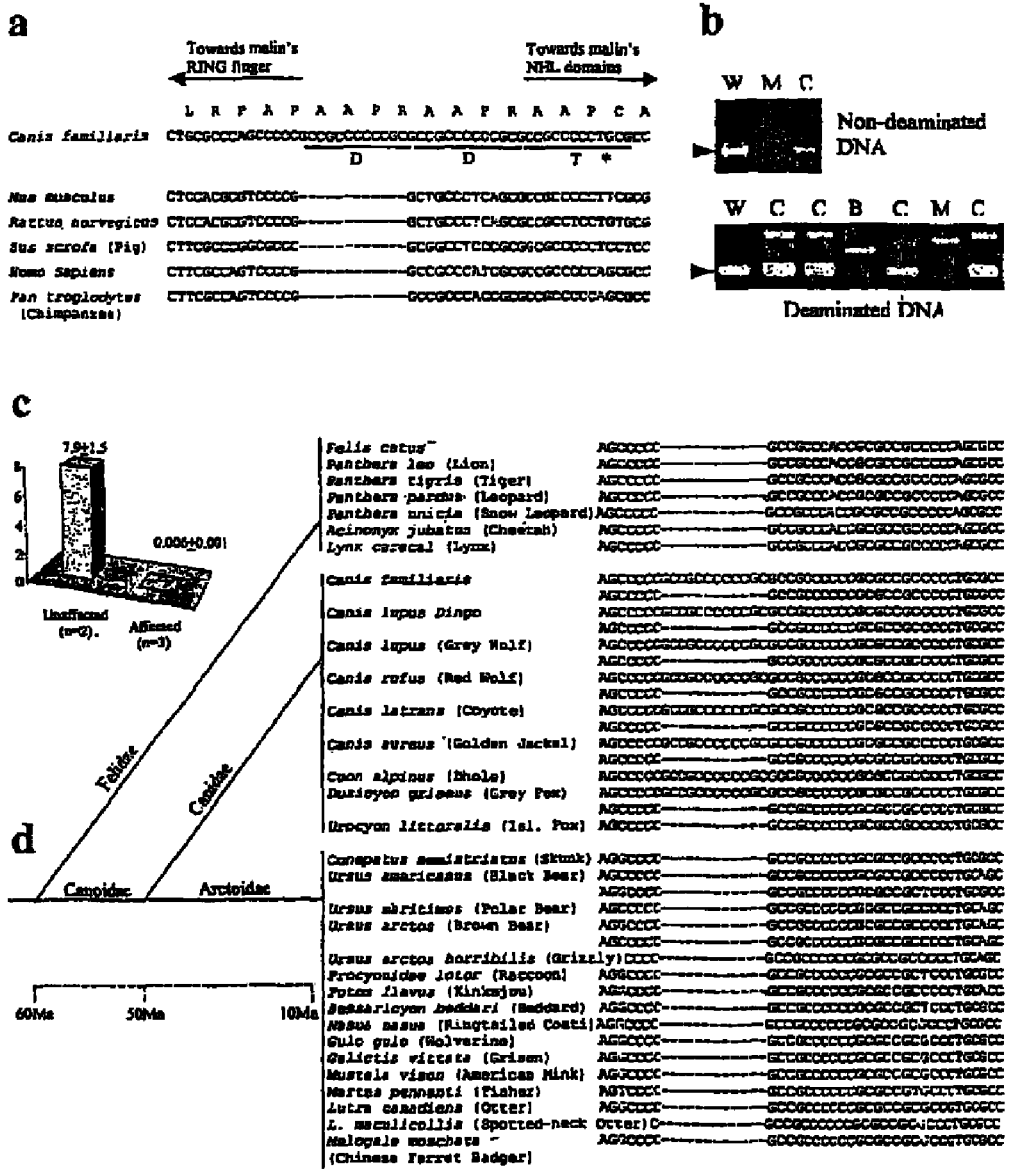

FIG. 10 shows the evolution of the EPM2B dodecamer polymorphism with the Canidae family of carnivores, presence of an expansion mutation in a non-MWHD epileptic dog, and the inactivating effect of expansions on EPM2B mRNA. a, Canine EPM2B dodecamer repeat sequence and orthologues; D, exact repeats; T, imperfect repeat (asterisk); red nucleotides, differences with the canine sequence in the repeat region. b, EPM2B expansion mutation associated with myoclonic epilepsy in dogs; W, wild-type; M, affected MWHD; B, affected Basset Hound; C, several unaffected carrier MWHD; arrowheads, normal alleles; all other bands, expanded mutant alleles; note how deamination greatly improves PCR detection of expanded alleles even in the presence of the normal sequence. c, EPM2B amounts (normalized against Gapdh) in skeletal muscle from affected MWHD and controls using real-time quantitative RT-PCR (SYBR Green detection; Supplementary Methods). d, Evolution of the dodecamer polymorphism; the D sequence is not present in feline species; it is present in all canoids: as a single copy in arctoids, and in polymorphic state with one or two copies in canids; both alleles are shown in heterozygous individuals (two sequence rows); all extant carnivores shown appeared sometime after 10 million years ago (Ma).

DETAILED DESCRIPTION OF THE INVENTION

Figure 2A:
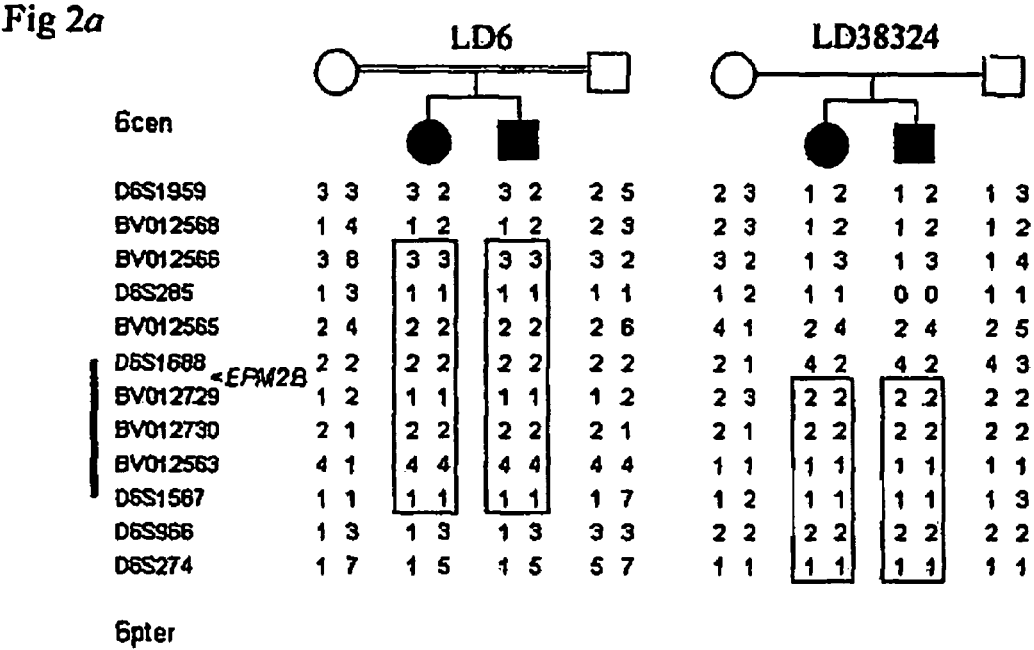

Previous studies by the inventors suggested that ~70% of LD patients carry recessive mutations in the EPM2A gene on chromosome 6q24 (6,7,14). To identify the causative gene(s) in the remaining patients, the inventors initially performed linkage and homozygosity mapping on a subset of the non-EPM2A LD families (LD6, LD7, LD27, LD28) originating from a French-Canadian (F-C) isolate (15) (Table 1). This approach led to the localization of a second LD locus (EPM2B) to a 2.2 Mb region on chromosome 6p22.3 (FIG. 1). All affected individuals from these F-C families were found to be homozygous for a rare haplotype across the entire critical interval (FIG. 2a). To further refine the locus, five additional LD families having multiply affected siblings were examined using every microsatellite marker that could be developed from the DNA sequence encompassing the critical region. In four families, all affected individuals were homozygous for all markers across the critical interval. In one family (LD38324), however, the chain of homozygosity in two affected individuals extended only partially into the critical region allowing reduction of the EPM2B locus to 840 kb between D6S1688 and D6S1567 (FIGS. 1 and 2*a*).

I. Nucleic Acid Molecules of the Invention

As hereinbefore mentioned, the present invention relates to isolated nucleic acid molecules that are involved in Lafora's disease. The term "isolated" refers to a nucleic acid substantially free of cellular material or culture medium when produced by recombinant DNA techniques, or chemical precursors, or other chemicals when chemically synthesized. The term "nucleic acid" is intended to include DNA and RNA and can be either double stranded or single stranded.

Broadly stated, the present invention provides an isolated nucleic acid molecule encoding a protein containing a zinc finger of the RING type in the N-terminal portion and 6 NHL-repeat domains in the C-terminal portion which is associated with Lafora's disease. The isolated nucleic acid molecule is preferably the EPM2B gene associated with Lafora's disease. In an embodiment of the invention, the isolated nucleic acid molecule has a sequence as shown in SEQ ID NO:1 (FIG. 6A) or SEQ ID NO:3 (FIG. 7A).

The nucleic acid sequences shown in SEQ ID NOS:1 and 3 (or FIGS. 6A and 7A, respectively) as well as the mutated sequences specified in Table 1 or in Example 3 can be collectively referred to herein as "the nucleic acid molecules of the invention". The amino acid sequences shown in SEQ ID NOS:2 and 4 (or FIGS. 6B and 7B, respectively) as well as the mutated sequences specified in Table 1 can be collectively referred to herein as the "proteins of the invention".

Preferably, the purified and isolated nucleic acid molecule comprises (a) a nucleic acid sequence as shown in SEQ ID NO:1 (FIG. 6A) or SEQ ID NO:3 (FIG. 7A), wherein T can also be U;

(b) a nucleic acid sequence complementary to (a);

(c) a nucleic acid sequence that has substantial sequence homology to a nucleic acid sequence of (a) or (b);

(d) a nucleic acid sequence that is an analog of a nucleic acid sequence of (a), (b) or (c); or (e) a nucleic acid sequence that hybridizes to a nucleic acid sequence of (a), (b), (c) or (d) under stringent hybridization conditions.

The term "sequence that has substantial sequence homology" means those nucleic acid sequences which have slight or inconsequential sequence variations from the sequences in (a) or (b), i.e., the sequences function in substantially the same manner and can be used to detect, study or treat Lafora's disease. The variations may be attributable to local mutations or structural modifications. Nucleic acid sequences having substantial homology include nucleic acid sequences having at least 65%, more preferably at least 85%, and most preferably 90-95% identity with the nucleic acid sequences as shown in SEQ ID NO:1 or SEQ ID NO:3.

"Sequence identity" can be calculated according to methods known in the art. Sequence identity is most preferably assessed by the algorithm of BLAST version 2.1 advanced search. BLAST is a series of programs that are available online at http://www.ncbi.nlm.nih.gov/BLAST. The advanced blast search (http://www.ncbi.nlm.nih.gov/blast/blast.cgi?Jform=1) is set to default parameters. (ie Matrix BLOSUM62; Gap existence cost 11; Per residue gap cost 1; Lambda ratio 0.85 default). References to BLAST searches are: Altschul, S. F., Gish, W., Miller, W., Myers, E. W. & Lipman, D. J. (1990) "Basic local alignment search tool." J. Mol. Biol. 215:403410; Gish, W. & States, D. J. (1993) "Identification of protein coding regions by database similarity search." Nature Genet. 3:266272; Madden, T. L., Tatusov, R. L. & Zhang, J. (1996) "Applications of network BLAST server" Meth. Enzymol. 266:131_141; Altschul, S. F., Madden, T. L., Schäffer, A. A., Zhang, J., Zhang, Z., Miller, W. & Lipman, D. J. (1997) "Gapped BLAST and PSI_BLAST: a new generation of protein database search programs." Nucleic Acids Res. 25:33893402; Zhang, J. & Madden, T. L. (1997) "PowerBLAST: A new network BLAST application for interactive or automated sequence analysis and annotation." Genome Res. 7:649656.

The term "sequence that hybridizes" means a nucleic acid sequence that can hybridize to a sequence of (a), (b), (c) or (d) under stringent hybridization conditions. Appropriate "stringent hybridization conditions" which promote DNA hybridization are known to those skilled in the art, or may be found in Current Protocols in Molecular Biology, John Wiley & Sons, N.Y. (1989), 6.3.1-6.3.6. The term "stringent hybridization conditions" as used herein means that conditions are selected which promote selective hybridization between two complementary nucleic acid molecules in solution. Hybridization may occur to all or a portion of a nucleic acid sequence molecule. The hybridizing portion is at least 50% the length with respect to one of the polynucleotide sequences encoding a polypeptide. In this regard, the stability of a nucleic acid duplex, or hybrids, is determined by the Tm, which in sodium containing buffers is a function of the sodium ion concentration, G/C content of labeled nucleic acid, length of nucleic acid probe (I), and temperature (Tm=81.5° C.−16.6 (Log 10 [Na+])+0.41(%(G+C)−600/l). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a greater than 95% identity, the final wash will be reduced by 5° C. Based on these considerations stringent hybridization conditions can be defined as: hybridization at 5× sodium chloride/sodium citrate (SSC)/5×Denhardt's solution/1.0% SDS at Tm (based on the above equation) −5° C., followed by a wash of 0.2×SSC/0.1% SDS at 60° C.

The term "a nucleic acid sequence which is an analog" means a nucleic acid sequence which has been modified as compared to the sequence of (a), (b) or (c) wherein the modification does not alter the utility of the sequence as described herein. The modified sequence or analog may have improved properties over the sequence shown in (a), (b) or (c). One example of a modification to prepare an analog is to replace one of the naturally occurring bases (i.e. adenine, guanine, cytosine or thymidine) of the sequence shown in SEQ ID NO:1 or 3, with a modified base such as such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule shown in SEQ ID NO:1 or SEQ ID NO:3. For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

It will be appreciated that the invention includes nucleic acid molecules encoding truncations of proteins of the invention, and analogs and homologs of proteins of the invention and truncations thereof, as described below. It will further be appreciated that variant forms of nucleic acid molecules of the invention which arise by alternative splicing of an mRNA corresponding to a cDNA of the invention are encompassed by the invention.

Isolated and purified nucleic acid molecules having sequences which differ from the nucleic acid sequence of the invention due to degeneracy in the genetic code are also within the scope of the invention. Such nucleic acids encode functionally equivalent proteins but differ in sequence from the above mentioned sequences due to degeneracy in the genetic code.

The invention also includes an isolated nucleic molecule that has a mutation as compared to the nucleic acid molecule shown in SEQ ID NO:1 (FIG. 6A) or SEQ ID NO:3 (FIG. 7A), wherein said mutation is associated with Lafora's disease. In a preferred embodiment, the mutation is selected from one of the mutations shown in Table 1 or the canine mutation described in Example 3.

Nucleic acid molecules from the EPM2B gene or mutated forms thereof can be isolated by preparing a labelled nucleic acid probe based on all or part of the nucleic acid sequences as shown in SEQ ID NO:1 (FIG. 6A) and SEQ ID NO:3 (FIG. 7A) or a mutated sequence shown in Table 1, and using this labelled nucleic acid probe to screen an appropriate DNA library (e.g. a cDNA or genomic DNA library). Nucleic acids isolated by screening of a cDNA or genomic DNA library can be sequenced by standard techniques.

Nucleic acid molecules of the invention can also be isolated by selectively amplifying a nucleic acid using the polymerase chain reaction (PCR) methods and cDNA or genomic DNA. It is possible to design synthetic oligonucleotide primers from the nucleic acid molecules as shown in SEQ ID NO:1 (FIG. 6A) and SEQ ID NO:3 (FIG. 7A) or a mutated sequence shown in Table 1, for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294-5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention which is RNA can be isolated by cloning a cDNA encoding a novel protein of the invention into an appropriate vector which allows for transcription of the cDNA to produce an RNA molecule which encodes the malin protein. For example, a cDNA can be cloned downstream of a bacteriophage promoter, (e.g. a T7 promoter) in a vector, cDNA can be transcribed in vitro with T7 polymerase, and the resultant RNA can be isolated by standard techniques.

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

The initiation codon and untranslated sequences of the nucleic acid molecules of the invention may be determined using currently available computer software designed for the purpose, such as PC/Gene (IntelliGenetics Inc., Calif.). Regulatory elements can be identified using conventional techniques. The function of the elements can be confirmed by using these elements to express a reporter gene which is operatively linked to the elements. These constructs may be introduced into cultured cells using standard procedures. In addition to identifying regulatory elements in DNA, such constructs may also be used to identify proteins interacting with the elements, using techniques known in the art.

The sequence of a nucleic acid molecule of the invention may be inverted relative to its normal presentation for transcription to produce an antisense nucleic acid molecule. Preferably, an antisense sequence is constructed by inverting a region preceding the initiation codon or an unconserved region. In particular, the nucleic acid sequences contained in the nucleic acid molecules of the invention or a fragment thereof, preferably a nucleic acid sequence shown in SEQ ID NO:1 (FIG. 6A) and SEQ ID NO:3 (FIG. 7A) or a mutated sequence shown in Table 1 may be inverted relative to its normal presentation for transcription to produce antisense nucleic acid molecules.

The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The invention also provides nucleic acids encoding fusion proteins comprising a novel protein of the invention and a selected protein, or a selectable marker protein (see below).

II. Novel Proteins of the Invention

The invention further includes an isolated protein encoded by the nucleic acid molecules of the invention. Within the context of the present invention, a protein of the invention may include various structural forms of the primary protein which retain biological activity.

Broadly stated, the present invention provides an isolated protein containing a zinc finger of the RING type in the N-terminal half and 6 NHL-repeat domains in the C-terminal direction which is associated with Lafora's disease. Preferably, the zinc-binding RING-finger motif ($C-X_2-C-X_{16}-C-X_1-H-X_2C-X_2-C-X_{14}-C-X_2-C$) is located between residues 26-71 of the malin protein shown in FIG. 6B. The presence of a RING finger is predictive of an E3 ubiquitin ligase function. Therefore, in a preferred embodiment, the protein has a ubiquitin ligase function.

In a specific embodiment of the invention, the protein has the amino acid sequence as shown in SEQ ID NO:2 (FIG. 6B) (human EPM2B). In another embodiment, the protein has the amino acid sequence shown in SEQ ID NO:4 (FIG. 7B) (canine EPM2B).

In addition to full length amino acid sequences the proteins of the present invention also include truncations of the protein, and analogs, and homologs of the protein and truncations thereof as described herein. Truncated proteins may comprise peptides of at least fifteen amino acid residues.

Analogs of the protein having the amino acid sequence shown in SEQ ID NO:2 (FIG. 6B) or SEQ ID NO:4 (FIG. 7B) and/or truncations thereof as described herein, may include, but are not limited to an amino acid sequence containing one or more amino acid substitutions, insertions, and/or deletions. Amino acid substitutions may be of a conserved or non-conserved nature. Conserved amino acid substitutions involve replacing one or more amino acids of the proteins of the invention with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

One or more amino acid insertions may be introduced into the amino acid sequences shown in SEQ ID NO:2 (FIG. 6B) or SEQ ID NO:4 (FIG. 7B). Amino acid insertions may consist of single amino acid residues or sequential amino acids ranging from 2 to 15 amino acids in length. For example, amino acid insertions may be used to destroy target sequences so that the protein is no longer active. This procedure may be used in vivo to inhibit the activity of a protein of the invention.

Deletions may consist of the removal of one or more amino acids, or discrete portions from the amino acid sequence shown in SEQ ID NO:2 (FIG. 6B) or SEQ ID NO:4 (FIG. 7B). The deleted amino acids may or may not be contiguous. The lower limit length of the resulting analog with a deletion mutation is about 10 amino acids, preferably 100 amino acids.

Analogs of a protein of the invention may be prepared by introducing mutations in the nucleotide sequence encoding the protein. Mutations in nucleotide sequences constructed for expression of analogs of a protein of the invention must preserve the reading frame of the coding sequences. Furthermore, the mutations will preferably not create complementary regions that could hybridize to produce secondary mRNA structures, such as loops or hairpins, which could adversely affect translation of the receptor mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site specific mutagenesis procedures may be employed to provide an altered gene having particular codons altered according to the substitution, deletion, or insertion required. Deletion or truncation of a protein of the invention may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

The proteins of the invention also include homologs of the amino acid sequence shown in SEQ ID NO:2 (FIG. 6B) or SEQ ID NO:4 (FIG. 7B) and/or truncations thereof as described herein. Such homologs are proteins whose amino acid sequences are comprised of amino acid sequences that hybridize under stringent hybridization conditions (see discussion of stringent hybridization conditions herein) with a probe used to obtain a protein of the invention. Preferably, homologs of a protein of the invention will have a tyrosine phosphatase region which is characteristic of the protein.

A homologous protein includes a protein with an amino acid sequence having at least 70%, preferably 80-90% identity with the amino acid sequence as shown in SEQ ID NO:2 (FIG. 6B) or SEQ ID NO:4 (FIG. 7B). Sequence identity is as previously defined herein.

The invention also contemplates isoforms of the proteins of the invention. An isoform contains the same number and kinds of amino acids as a protein of the invention, but the isoform has a different molecular structure. The isoforms contemplated by the present invention are those having the same properties as a protein of the invention as described herein.

The invention also includes an isolated protein that has a mutation as compared to the amino acid sequence shown in SEQ ID NO:2 (FIG. 6B) or SEQ ID NO:4 (FIG. 7B), wherein said mutation is associated with Lafora's disease. In a preferred embodiment, the mutation is selected from one of the mutations shown in Table 1 or the canine mutation described in Example 3.

The present invention also includes a protein of the invention conjugated with a selected protein, or a selectable marker protein (see below) to produce fusion proteins. Additionally, immunogenic portions of a protein of the invention are within the scope of the invention.

The proteins of the invention (including truncations, analogs, mutants etc.) may be prepared using recombinant DNA methods. Accordingly, the nucleic acid molecules of the present invention having a sequence which encodes a protein of the invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

The invention further provides a recombinant expression vector comprising a DNA nucleic acid molecule of the invention cloned into the expression vector in an antisense orientation. That is, the DNA molecule is operatively linked to a regulatory sequence in a manner which allows for expression, by transcription of the DNA molecule, of an RNA molecule which is antisense to a nucleotide sequence comprising the nucleotides as shown SEQ ID NO:1 or SEQ ID NO:3. Regulatory sequences operatively linked to the antisense nucleic acid can be chosen which direct the continuous expression of the antisense RNA molecule.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is nionitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of a target recombinant protein by acting as a ligand in affinity purification. For example, a proteolytic cleavage site may be added to the target recombinant protein to allow separation of the recombinant protein from the fusion moiety subsequent to purification of the fusion protein.

Recombinant expression vectors can be introduced into host cells to produce a transformed host cell. The term "transformed host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as E. coli, insect cells (using baculovirus), yeast cells or mammalian cells. Other suitable host cells can be found in Goeddel, Gene Expression Technology: Methods in Enzymology 185, Academic Press, San Diego, Calif. (1991).

The proteins of the invention may also be prepared by chemical synthesis using techniques well known in the chemistry of proteins such as solid phase synthesis (Merrifield, 1964, J. Am. Chem. Assoc. 85: 2149-2154) or synthesis in homogenous solution (Houbenweyl, 1987, Methods of Organic Chemistry, ed. E. Wansch, Vol. 15 I and II, Thieme, Stuttgart).

III. Applications

The present invention includes all uses of the nucleic acid molecule and proteins of the invention including, but not limited to, the preparation of antibodies and antisense oligonucleotides, the preparation of experimental systems to study EPM2B and mutated forms thereof, the isolation of substances that modulate EPM2B expression and/or activity as well as the use of the EPM2B nucleic acid sequences and proteins and modulators thereof in diagnostic and therapeutic applications. Some of the uses are further described below.

A. Diagnostic Applications

As previously mentioned, the present inventors have determined that the gene EPM2B is mutated in people and canids with Lafora's disease. As a result, the present invention also includes a method of detecting Lafora's disease by detecting a mutation in the EPM2B gene or protein.

The term "mutation" means any change or difference in the nucleic acid or protein sequence of EPM2B as compared to the wild type sequence. Mutations include, but are not limited to, nonsense mutations, missense mutations, frameshift mutations, rearrangement mutations, insertion mutations and deletion mutations.

The sample can be any sample containing the EPM2B gene or protein including, but not limited to, biological fluids (such as blood, urine, cerebrospinal fluid, tears, saliva), tissues, tissue extracts, cells and cell extracts.

(i) Detecting Mutations in the Nucleic Acid Sequence

In one embodiment, the present invention provides a method for detecting Lafora's disease comprising detecting a mutation in the EPM2B gene in a sample obtained from an animal, preferably a mammal, more preferably a human or canid.

Table 1 summarizes some of the mutations found in human EPM2B in patients with Lafora's disease. To date, 21 different DNA sequence alterations have been found in EPM2B in 39 families including 8 deletions and 1 insertion leading to frame-shifts, 8 missense, and 1 non-sense change. Screening assays can be developed for each of the mutations.

The most common mutation identified in seven families is a homozygous 205C→G transition resulting in a proline to alanine change in the RING-finger domain. Accordingly, in one embodiment, the present invention provides a method of detecting Lafora's disease comprising detecting a C→G mutation at position 205 in the EPM2B gene (SEQ ID NO:1).

Another mutation observed in the four consanguineous F-C families used in the original linkage study all carried a homozygous 76T→A change producing a cysteine-to-serine alteration in one of the 7 conserved cysteine residues that are critical for the zinc-binding ability of the RING-finger domain. Accordingly, in another embodiment, the present invention provides a method of detecting Lafora's disease comprising detecting a T→A mutation at position 76 in the EPM2B gene (SEQ ID NO:1).

Figure 2B:
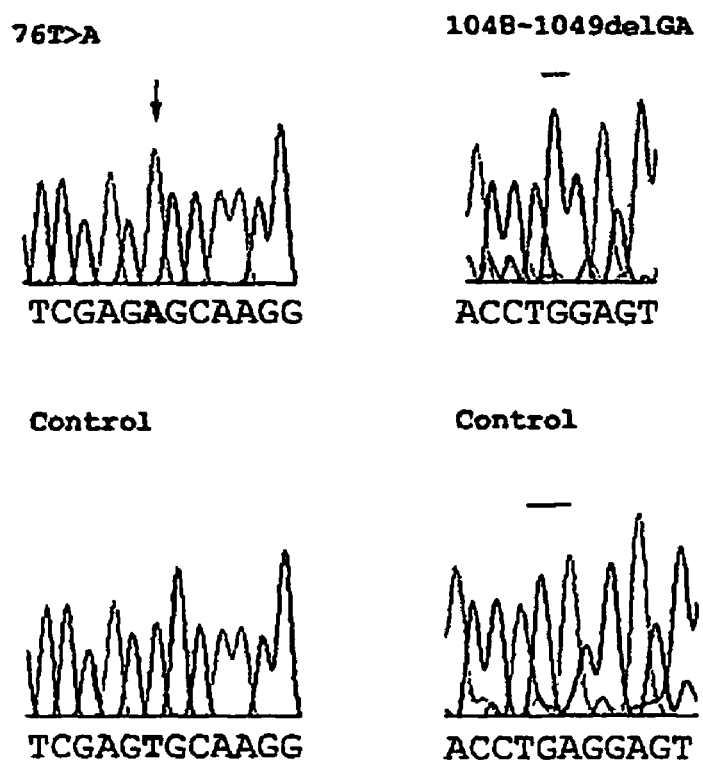

Another mutation was observed in the LD38324 family that was critical in refining the EPM2B locus (FIG. 2a) which was a homozygous 2-bp deletion (1048-1049delGA) leading to a frame-shift mutation in the fifth NHL-domain (FIG. 2b). Accordingly, in a further embodiment, the present invention provides a method of detecting Lafora's disease comprising detecting a deletion of GA at positions 1048 and 1049 in the EPM2B gene (SEQ ID NO:1).

As described in Example 3, the inventors have also discovered a mutation in the EPM2B gene in dogs with Lafora's disease. In particular, all affected dogs studied had a bi-allelic expansion of a dodecamer repeat, termed D, and having the sequence GCCGCCCCCCGC (SEQ ID NO: 5) that starts at nucleotide number 1001 of canine EPM2B sequence shown in SEQ ID NO: 3. The inventors have shown that this 12 nucleotide repeat is specific to the canid superfamily, which includes dogs, wolves, foxes, coyotes, and jackals, and have shown that this repeat predisposes dogs to a massive sequence expansion, which is destructive to the EPM2B gene and causes Lafora disease. The inventors have thus discovered that canids, including dogs, are predisposed to Lafora Epilepsy. Accordingly, the invention further provides a method of detecting Lafora's disease in a canid comprising detecting a repeat of the sequence GCCGCCCCCCGC (SEQ ID NO: 5) which starts at nucleotide number 1001 in the canine sequence of EPM2B (SEQ ID NO: 3). In one embodiment, the method involves detecting at least 3 repeats, preferably at least 10 repeats, more preferably from about 14 to about 26 repeats in SEQ ID NO: 5.

One skilled in the art will appreciate that many suitable methods, in addition to and including the ones discussed in the examples, can be used to detect mutations in the EPM2B gene. Detection methods that can be used include, but are not limited to, polymerase chain reaction (PCR), reverse transcriptase PCR, direct sequencing electrophoretic mobility, nucleic acid hybridization, fluorescent in situ hybridization, denaturing high performance liquid chromatography, DNA chip technologies and mass spectroscopy. In one example, in order to isolate nucleic acids from the Lafora's disease gene in a sample, one can prepare nucleotide probes from the nucleic acid sequences of the invention. In addition, the nucleic acid probes described herein can also be used. A nucleotide probe may be labelled with a detectable marker such as a radioactive label which provides for an adequate signal and has sufficient half life such as $^{32}P$, $^{3}H$, $^{14}C$ or the like. Other detectable markers which may be used include antigens that are recognized by a specific labelled antibody, fluorescent compounds, enzymes, antibodies specific for a labelled antigen, and chemiluminescent compounds. An appropriate label may be selected having regard to the rate of hybridization and binding of the probe to the nucleotide to be detected and the amount of nucleotide available for hybridization.

Accordingly, the present invention also relates to a method of detecting the presence of a nucleic acid molecule from the EPM2B gene in a sample comprising contacting the sample under hybridization conditions with one or more of nucleotide probes which hybridize to the nucleic acid molecules and are labelled with a detectable marker, and determining the degree of hybridization between the nucleic acid molecule in the sample and the nucleotide probes.

Hybridization conditions which may be used in the methods of the invention are known in the art and are described for example in Sambrook J, Fritch E F, Maniatis T. In: Molecular Cloning, A Laboratory Manual, 1989. (Nolan C, Ed.), Cold Spring Harbor Laboratory Press, Cold Spring Harbor, N.Y. The hybridization product may be assayed using techniques known in the art. The nucleotide probe may be labelled with a detectable marker as described herein and the hybridization product may be assayed by detecting the detectable marker or the detectable change produced by the detectable marker.

Prior to hybridizing a sample with DNA probes, the sample can be treated with primers that flank the EPM2B gene in order to amplify the nucleic acid sequences in the sample. The primers used may be the ones described in the present application. In addition, the sequence of the EPM2B gene provided herein also permits the identification and isolation, or synthesis of new nucleotide sequences which may be used as primers to amplify a nucleic acid molecule of the invention, for example in the polymerase chain reaction (PCR) which is discussed in more detail below. The primers may be used to amplify the genomic DNA of other species. The PCR amplified sequences can be examined to determine the relationship between the genes of various species.

The length and bases of the primers for use in the PCR are selected so that they will hybridize to different strands of the desired sequence and at relative positions along the sequence such that an extension product synthesized from one primer when it is separated from its template can serve as a template for extension of the other primer into a nucleic acid of defined length. Primers which may be used in the invention are oligonucleotides i.e. molecules containing two or more deoxyribonucleotides of the nucleic acid molecule of the invention which occur naturally as in a purified restriction endonuclease digest or are produced synthetically using techniques known in the art such as for example phosphotriester and phosphodiester methods (See Good et al Nucl. Acid Res 4:2157, 1977) or automated techniques (See for example, Conolly, B. A. Nucleic Acids Res. 15:15 (7): 3131, 1987). The primers are capable of acting as a point of initiation of synthesis when placed under conditions which permit the synthesis of a primer extension product which is complementary to the DNA sequence of the invention i.e. in the presence of nucleotide substrates, an agent for polymerization such as DNA polymerase and at suitable temperature and pH. Preferably, the primers are sequences that do not form secondary structures by base pairing with other copies of the primer or sequences that form a hair pin configuration. The primer preferably contains between about 7 and 25 nucleotides.

The primers may be labelled with detectable markers which allow for detection of the amplified products. Suitable detectable markers are radioactive markers such as P-32, S-35, I-125, and H-3, luminescent markers such as chemiluminescent markers, preferably luminol, and fluorescent markers, preferably dansyl chloride, fluorescein-5-isothiocyanate, and 4-fluor-7-nitrobenz-2-axa-1,3 diazole, enzyme markers such as horseradish peroxidase, alkaline phosphatase, β-galactosidase, acetylcholinesterase, or biotin.

It will be appreciated that the primers may contain non-complementary sequences provided that a sufficient amount of the primer contains a sequence which is complementary to a nucleic acid molecule of the invention or oligonucleotide fragment thereof, which is to be amplified. Restriction site linkers may also be incorporated into the primers allowing for digestion of the amplified products with the appropriate restriction enzymes facilitating cloning and sequencing of the amplified product.

In an embodiment of the invention a method of determining the presence of a nucleic acid molecule of the invention is provided comprising treating the sample with primers which are capable of amplifying the nucleic acid molecule or a predetermined oligonucleotide fragment thereof in a polymerase chain reaction to form amplified sequences, under conditions which permit the formation of amplified sequences and, assaying for amplified sequences.

The polymerase chain reaction refers to a process for amplifying a target nucleic acid sequence as generally described in Innis et al, Academic Press, 1990 in Mullis el al., U.S. Pat. No. 4,863,195 and Mullis, U.S. Pat. No. 4,683,202 which are incorporated herein by reference. Conditions for amplifying a nucleic acid template are described in M. A. Innis and D. H. Gelfand, PCR Protocols, A Guide to Methods and Applications M. A. Innis, D. H. Gelfand, J. J. Sninsky and T. J. White eds, pp 3-12, Academic Press 1989, which is also incorporated herein by reference.

The amplified products can be isolated and distinguished based on their respective sizes using techniques known in the art. For example, after amplification, the DNA sample can be separated on an agarose gel and visualized, after staining with ethidium bromide, under ultra violet (UW) light. DNA may be amplified to a desired level and a further extension reaction may be performed to incorporate nucleotide derivatives having detectable markers such as radioactive labelled or biotin labelled nucleoside triphosphates. The primers may also be labelled with detectable markers as discussed above. The detectable markers may be analyzed by restriction and electrophoretic separation or other techniques known in the art.

The conditions which may be employed in the methods of the invention using PCR are those which permit hybridization and amplification reactions to proceed in the presence of DNA in a sample and appropriate complementary hybridization primers. Conditions suitable for the polymerase chain reaction are generally known in the art. For example, see M. A. Innis and D. H. Gelfand, PCR Protocols, A guide to Methods and Applications M. A. Innis, D. H. Gelfand, J. J. Sninsky and T. J. White eds, pp 3-12, Academic Press 1989, which is incorporated herein by reference. Preferably, the PCR utilizes polymerase obtained from the thermophilic bacterium *Thermus aquatics* (Taq polymerase, GeneAmp Kit, Perkin Elmer Cetus) or other thermostable polymerase may be used to amplify DNA template strands.

It will be appreciated that other techniques such as the Ligase Chain Reaction (LCR) and NASBA may be used to amplify a nucleic acid molecule of the invention (Barney in "PCR Methods and Applications", August 1991, Vol. 1 (1), page 5, and European Published Application No. 0320308, published Jun. 14, 1989, and U.S. Pat. No. 5,130,238 to Malek).

In some embodiments of the present invention, mutations in the sequences of the invention may be detected by the direct sequencing of nucleic acid molecules. Techniques for the direct sequencing of DNA are well known in the art. In one embodiment of the invention, mutations may be detected cycle sequencing, which may include the use of a thermostable polymerase enzyme, a sequencing primer, dNTPs and limiting amounts of chain terminating fluorescently or radioactively labelled ddNTPs. Polyacrylamide gel electrophoresis or another technique such as capillary electrophoresis may be used to separate the products of the sequencing reactions followed by the detection of the fluorescent or radioactive labels. In one example of this embodiment of the invention, mutations in EMP2B could be determined using automated sequencing on an Applied Biosystems 3700 DNA Analyzer or 3730xl DNA Analyzer™. Mutations may be identified by comparing the sequence of a patient to that of a wildtype individual or to reference sequences found in the public databases.

Mutations in EMP2B may also be detected using the Invader™ genotyping system which uses a Cleavase™ Fragment Length Polymorphism (CFLP) assay as disclosed in U.S. Pat. No. 5,888,780 and available from Third Wave™ Technologies in Madison, Wis.

Other embodiments of the invention contemplate the use of DNA chip technologies for the detection of mutations within the EMP2B gene. Among other applications, DNA chip technologies allow for the identification of mutations within the sequences of the intention through the analysis of the hybridisation patterns of a nucleic acid sample onto a high-density spatially addressable microarray of predetermined sequences. One example of a DNA chip technology suitable for the identification of mutations is the sequences of the invention is the Affymatrix GeneChip™ system, as disclosed in U.S. Pat. No. 6,045,996. This system uses photolithography and solid-phase chemistry to produce high density arrays containing hundreds of thousands of oligonucleotide probes. Genechips™ may be designed so as to facilitate the re-sequencing of a particular sequence, allowing for the identification of specific mutations. Computer based image analysis of the hybridisation patterns enables automatic base calling, and the incorporation of quality control measures within the analysis.

One skilled in the art will be aware that Southern blotting or Northern blotting may be used to detect pathogenic deletions or rearrangements within or near the sequences of the invention. Fluorescence In Situ Hybridization (FISH), fiber-FISH or other high-resolution cytogenetic methods may similarly be used for the detection of rearrangements or deletions that disrupt the sequences of the invention.

Another technique for the detection of mutations is denaturing HPLC analysis. Accordingly, one embodiment of the invention includes the use of a Transgenomic Wave™ machine for the dHPLC analysis of nucleic acids for the identification of heterozygous mutations or polymorphisms within the sequences of the invention.

The invention also contemplates the use of mass spectroscopy for the genotyping of mutations. Mutant and wildtype nucleic acid molecules may differ in mass due to the different composition of wildtype and mutant sequences, allowing for the identification of mutations on the basis of the molecular mass of different nucleotide sequences. The use of mass spectroscopy, and in particular Matrix Assisted Laser Desorption Ionisation Time of Flight (MALDI-TOF) mass spectroscopy for the genotyping of mutations is well known by those skilled in the relevant art. For example, U.S. Pat. No. 6,043,031 describes a fast and highly accurate mass spectrometer based process for detecting a particular nucleic acid sequence. The MassARRAY™ platform from SEQUENOM™ is an example of a commercially available system capable of genotyping single nucleotide polymorphisms and detecting the mutations as described in the present invention.

(ii) Detecting the Malin Protein

In another embodiment, the present invention provides a method for detecting Lafora's disease comprising determining if the malin protein is present or mutated in a sample from a mammal, preferably a human or dog, suspected of having Lafora's disease.

The malin protein of the present invention may be detected in a biological sample using antibodies that are specific for malin using various immunoassays that are discussed below. Antibodies that only react with mutated malin would be useful as diagnostic agents to detect Lafora's disease. As such, antibodies would be prepared that bind only a mutated region of the protein.

Conventional methods can be used to prepare the antibodies. For example, by using a peptide from the malin protein of the invention, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495497 (1975)) as well as other techniques such as the human B-cell hybridoma technique (Kozbor et al., Immunol. Today 4, 72 (1983)), the EBV hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)]. Hybridoma cells can be screened immunochemically for production of antibodies specifically reactive with the peptide and the monoclonal antibodies can be isolated. Therefore, the invention also contemplates hybridoma cells secreting monoclonal antibodies with specificity for a protein of the invention.

The term "antibody" as used herein is intended to include fragments thereof which also specifically react with a protein, of the invention, or peptide thereof. Antibodies can be fragmented using conventional techniques and the fragments screened for utility in the same manner as described above. For example, F(ab')$_2$ fragments can be generated by treating antibody with pepsin. The resulting F(ab')$_2$ fragment can be treated to reduce disulfide bridges to produce Fab' fragments.

Chimeric antibody derivatives, i.e., antibody molecules that combine a non human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes a malin protein (see, for example, Morrison et al., Proc. Natl Acad. Sci. U.S.A. 81, 6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, reactive against a protein of the invention may also be generated by screening expression libraries encoding immunoglobulin genes, or portions thereof, expressed in bacteria with peptides produced from the nucleic acid molecules of the present invention. For example, complete Fab fragments, VH regions and FV regions can be expressed in bacteria using phage expression libraries (See for example Ward et al., Nature 341, 544-546: (1989); Huse et al., Science 246, 1275-1281 (1989); and McCafferty et al. Nature 348, 552-554 (1990)).

Antibodies may also be prepared using DNA immunization. For example, an expression vector containing a nucleic acid of the invention (as described above) may be injected into a suitable animal such as mouse. The protein of the invention will therefore be expressed in vivo and antibodies will be induced. The antibodies can be isolated and prepared as described above for protein immunization.

The antibodies may be labelled with a detectable marker including various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include S-35, Cu-64, Ga-67, Zr-89, Ru-97, Tc-99m, Rh-105, Pd-109, In-111, I-123, I-125, I131, Re-186, Au-198, Au-199, Pb-203, At-211, Pb-212 and Bi-212. The antibodies may also be labelled or conjugated to one partner of a ligand binding pair. Representative examples include avidin-biotin and riboflavin-riboflavin binding protein. Methods for conjugating or labelling the antibodies discussed above with the representative labels set forth above may be readily accomplished using conventional techniques.

The antibodies reactive against proteins of the invention (e.g. enzyme conjugates or labelled derivatives) may be used to detect a protein of the invention in various samples, for example they may be used in any known immunoassays which rely on the binding interaction between an antigenic determinant of a protein of the invention and the antibodies. Examples of such assays are radioimmunoassays, enzyme immunoassays (e.g. ELISA), immunofluorescence, immunoprecipitation, latex agglutination, hemagglutination, and histochemical tests. Thus, the antibodies may be used to identify or quantify the amount of a protein of the invention in a sample in order to diagnose the presence of Lafora's disease.

In a method of the invention a predetermined amount of a sample or concentrated sample is mixed with antibody or labelled antibody. The amount of antibody used in the process is dependent upon the labelling agent chosen. The resulting protein bound to antibody or labelled antibody may be isolated by conventional isolation techniques, for example, salting out, chromatography, electrophoresis, gel filtration, fractionation, absorption, polyacrylamide gel electrophoresis, agglutination, or combinations thereof.

The sample or antibody may be insolubilized, for example, the sample or antibody can be reacted using known methods with a suitable carrier. Examples of suitable carriers are Sepharose or agarose beads. When an insolubilized sample or antibody is used protein bound to antibody or unreacted antibody is isolated by washing. For example, when the sample is blotted onto a nitrocellulose membrane, the antibody bound to a protein of the invention is separated from the unreacted antibody by washing with a buffer, for example, phosphate buffered saline (PBS) with bovine serum albumin (BSA).

When labelled antibody is used, the presence of malin can be determined by measuring the amount of labelled antibody bound to a protein of the invention in the sample or of the unreacted labelled antibody. The appropriate method of measuring the labelled material is dependent upon the labelling agent.

When unlabelled antibody is used in the method of the invention, the presence of malin can be determined by measuring the amount of antibody bound to the protein using substances that interact specifically with the antibody to cause agglutination or precipitation. In particular, labelled antibody against an antibody specific for a protein of the invention, can be added to the reaction mixture. The presence of a protein of the invention can be determined by a suitable method from among the already described techniques depending on the type of labelling agent. The antibody against an antibody specific for a protein of the invention can be prepared and labelled by conventional procedures known in the art which have been described herein. The antibody against an antibody specific for a protein of the invention may be a species specific anti-immunoglobulin antibody or monoclonal antibody, for example, goat anti-rabbit antibody may be used to detect rabbit antibody specific for a protein of the invention.

(iii) Kits

The reagents suitable for carrying out the methods of the invention may be packaged into convenient kits providing the necessary materials, packaged into suitable containers. Such kits may include all the reagents required to detect a nucleic acid molecule or protein of the invention in a sample by means of the methods described herein, and optionally suitable supports useful in performing the methods of the invention.

In one embodiment of the invention, the kit includes primers which are capable of amplifying a nucleic acid molecule of the invention or a predetermined oligonucleotide fragment thereof, all the reagents required to produce the amplified nucleic acid molecule or predetermined fragment thereof in the polymerase chain reaction, and means for assaying the amplified sequences. The kit may also include restriction enzymes to digest the PCR products. In another embodiment of the invention the kit contains a nucleotide probe which hybridizes with a nucleic acid molecule of the invention, reagents required for hybridization of the nucleotide probe with the nucleic acid molecule, and directions for its use. In a further embodiment of the invention the kit includes antibodies of the invention and reagents required for binding of the antibody to a protein of the invention in a sample.

The methods and kits of the present invention may be used to detect Lafora's disease. Samples which may be tested include bodily materials such as blood, urine, serum, tears, saliva, feces, tissues, cells and the like. In addition to human samples, samples may be taken from mammals such as non-human primates and canids such as dogs.

Before testing a sample in accordance with the methods described herein, the sample may be concentrated using techniques known in the art, such as centrifugation and filtration. For the hybridization and/or PCR-based methods described herein, nucleic acids may be extracted from cell extracts of the test sample using techniques known in the art.

B. EPM2B/Malin Modulator

In addition to antibodies and antisense oligonucleotides described above, other substances that modulate EPM2B expression or activity may also be identified, as well as substances that modulate mutated forms of malin.

(i) Substances that Bind Malin

Substances that affect malin activity can be identified based on their ability to bind to malin and/or mutated malin.

Substances which can bind with the malin of the invention may be identified by reacting the malin with a substance which potentially binds to malin, and assaying for complexes, for free substance, or for non-complexed malin, or for activation of malin. In particular, a yeast two hybrid assay system may be used to identify proteins which interact with malin (Fields, S. and Song, O., 1989, Nature, 340:245-247). Systems of analysis which also may be used include ELISA.

Accordingly, the invention provides a method of identifying substances which can bind with malin, comprising the steps of:

(a) reacting malin and a test substance, under conditions which allow for formation of a complex between the malin and the test substance, and (b) assaying for complexes of malin and the test substance, for free substance or for non complexed malin, wherein the presence of complexes indicates that the test substance is capable of binding malin.

The malin protein used in the assay may have the amino acid sequence shown in SEQ ID NO:2 (FIG. 6B) or SEQ ID NO:4 (FIG. 7B) or may be a mutated protein associated with LD as described herein or may be a fragment, analog, derivative, homolog or mimetic thereof as described herein.

Conditions which permit the formation of substance and malin complexes may be selected having regard to factors such as the nature and amounts of the substance and the protein.

The substance-protein complex, free substance or non-complexed proteins may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against malin or the substance, or labelled malin, or a labelled substance may be utilized. The antibodies, proteins, or substances may be labelled with a detectable substance as described above.

Malin, or the substance used in the method of the invention may be insolubilized. For example, malin or substance may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc.

The insolubilized protein or substance may be prepared by reacting the material with a suitable insoluble carrier using known chemical or physical methods, for example, cyanogen bromide coupling.

The proteins or substance may also be expressed on the surface of a cell using the methods described herein.

The invention also contemplates assaying for an antagonist or agonist of the action of malin.

It will be understood that the agonists and antagonists that can be assayed using the methods of the invention may act on one or more of the binding sites on the protein or substance including agonist binding sites, competitive antagonist binding sites, non-competitive antagonist binding sites or allosteric sites.

The invention also makes it possible to screen for antagonists that inhibit the effects of an agonist of malin. Thus, the invention may be used to assay for a substance that competes for the same binding site of malin.

(ii) Peptide Mimetics

The present invention also includes peptide mimetics of the malin and mutated malin proteins of the invention. For example, a peptide derived from a the mutated domain of malin will interact directly or indirectly with an associated molecule in such a way as to mimic the native binding of the mutated protein. Such peptides may include competitive inhibitors, enhancers, peptide mimetics, and the like. All of these peptides as well as molecules substantially homologous, complementary or otherwise functionally or structurally equivalent to these peptides may be used for purposes of the present invention.

"Peptide mimetics" are structures which serve as substitutes for peptides in interactions between molecules (See Morgan et al (1989), Ann. Reports Med. Chem. 24:243-252 for a review). Peptide mimetics include synthetic structures which may or may not contain amino acids and/or peptide bonds but retain the structural and functional features of a peptide, or enhancer or inhibitor of the invention. Peptide mimetics also include peptoids, oligopeptoids (Simon et al (1972) Proc. Natl. Acad, Sci USA 89:9367); and peptide libraries containing peptides of a designed length representing all possible sequences of amino acids corresponding to a peptide of the invention.

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

Peptides of the invention may also be used to identify lead compounds for drug development. The structure of the peptides described herein can be readily determined by a number of methods such as NMR and X-ray crystallography. A comparison of the structures of peptides similar in sequence, but differing in the biological activities they elicit in target molecules can provide information about the structure-activity relationship of the target. Information obtained from the examination of structure-activity relationships can be used to design either modified peptides, or other small molecules or lead compounds that can be tested for predicted properties as related to the target molecule. The activity of the lead compounds can be evaluated using assays similar to those described herein.

Information about structure-activity relationships may also be obtained from co-crystallization studies. In these studies, a peptide with a desired activity is crystallized in association with a target molecule, and the X-ray structure of the complex is determined. The structure can then be compared to the structure of the target molecule in its native state, and information from such a comparison may be used to design compounds expected to possess.

(iii) Drug Screening Methods

In accordance with one embodiment, the invention enables a method for screening candidate compounds for their ability to increase or decrease the activity of the mutated malin protein. The method comprises providing an assay system for assaying malin activity, assaying the activity in the presence or absence of the candidate or test compound and determining whether the compound has increased or decreased malin activity. Such compounds may be useful in treating Lafora's disease.

Accordingly, the present invention provides a method for identifying a compound that affects mutated malin protein activity or expression comprising:

(a) incubating a test compound with a malin protein or a nucleic acid encoding a malin protein; and (b) determining an amount of malin protein activity or expression and comparing with a control (i.e. in the absence of the test substance), wherein a change in the malin protein activity or expression as compared to the control indicates that the test compound has an effect on malin protein activity or expression.

In accordance with a further embodiment, the invention enables a method for screening candidate compounds for their ability to increase or decrease expression of a malin protein. The method comprises putting a cell with a candidate compound, wherein the cell includes a regulatory region of a malin gene operably joined to a reporter gene coding region, and detecting a change in expression of the reporter gene.

In one embodiment, the present invention enables culture systems in which cell lines which express the mutated malin gene are incubated with candidate compounds to test their effects on mutated malin expression. Such culture systems can be used to identify compounds which upregulate or downregulate malin expression or its function, through the interaction with other proteins.

Such compounds can be selected from protein compounds, chemicals and various drugs that are added to the culture medium. After a period of incubation in the presence of a selected test compound(s), the expression of mutated malin can be examined by quantifying the levels of malin mRNA using standard Northern blotting procedure, as described in the examples included herein, to determine any changes in expression as a result of the test compound. Cell lines transfected with constructs expressing malin can also be used to test the function of compounds developed to modify the protein expression.

C. Therapeutic Uses

As previously discussed, the EPM2B gene and malin of the invention is likely involved in Lafora's disease. Accordingly, the present invention provides a method of treating Lafora's disease comprising of administering to a cell or animal in need thereof, an effective amount of agent that modulates EPM2B/malin expression and/or activity. The present invention also provides a use of an agent that modulates EPM2B/malin expression and/or activity to treat Lafora's disease or to prepare a medicament to treat Lafora's disease.

The term "agent that modulates EPM2B/malin expression and/or activity" means any substance that can alter the expression and/or activity of the mutated EPM2B/malin found in the animal to be consistent with the wild type EPM2B/malin. Examples of agents which may be used to include administering: a nucleic acid molecule encoding wild type EPM2B; the wild type main protein as well as fragments, analogs, derivatives or homologs thereof; antibodies; antisense nucleic acids; peptide mimetics; and substances isolated using the screening methods described herein that can correct the mutation to result in EPM2B/malin levels and/or function consistent with a person without the disease.

The term "effective amount" as used herein means an amount effective, at dosages and for periods of time necessary to achieve the desired results.

The term "animal" as used herein includes all members of the animal kingdom, including humans and dogs.

In one embodiment, the invention provides a method of treating Lafora's disease by administering to a cell or animal an effective amount of an agent that modulates the expression or the biological activity of the mutated malin protein. The present invention also provides a use of an effective amount of an agent that modulates the expression or the biological activity of the mutated malin protein to treat Lafora's disease or to prepare a medicament to treat Lafora's disease. Substances that inhibit the activity of mutated malin include peptide mimetics, malin antagonists and certain antibodies to malin. Substances that inhibit the expression of the mutated EPM2B gene include antisense oligonucleotides to a mutated EPM2B nucleic acid sequence.

In accordance with another embodiment, the present invention enables gene therapy as a potential therapeutic approach to Lafora's disease, in which normal copies of the EPM2B gene are introduced into patients to successfully code for normal malin protein in several different affected cell types.

Retroviral vectors can be used for somatic cell gene therapy especially because of their high efficiency of infection and stable integration and expression. The targeted cells however must be able to divide and the expression of the levels of normal protein should be high. The full length normal EPM2B gene can be cloned into a retroviral vector and driven from its endogenous promoter or from the retroviral long terminal repeat or from a promoter specific for the target cell type of interest. Other viral vectors which can be used include adeno-associated virus, vaccinia virus, bovine papilloma virus, or a herpesvirus such as Epstein-Barr virus. Gene transfer could also be achieved using non-viral means requiring infection in vitro. This would include calcium phosphate, DEAE dextran, electroporation, cationic or anionic lipid formulations (liposomes) and protoplast fusion. Although these methods are available, many of these are lower efficiency.

Anti-sense based strategies can be employed to inhibit mutated EPM2B gene function and as a basis for therapeutic drug design. The principle is based on the hypothesis that sequence specific suppression of gene expression can be achieved by intracellular hybridization between mRNA and a complementary anti-sense species. It is possible to synthesize anti-sense strand nucleotides that bind the sense strand of RNA or DNA with a high degree of specificity. The formation of a hybrid RNA duplex may interfere with the processing/transport/translation and/or stability of a target mRNA.

Hybridization is required for an antisense effect to occur. Antisense effects have been described using a variety of approaches including the use of antisense oligonucleotides, injection of antisense RNA, DNA and transfection of antisense RNA expression vectors.

Therapeutic antisense nucleotides can be made as oligonucleotides or expressed nucleotides. Oligonucleotides are short single strands of DNA which are usually 15 to 20 nucleic acid bases long. Expressed nucleotides are made by an expression vector such as an adenoviral, retroviral or plasmid vector. The vector is administered to the cells in culture, or to a patient, whose cells then make the antisense nucleotide. Expression vectors can be designed to produce antisense RNA, which can vary in length from a few dozen bases to several thousand.

Antisense effects can be induced by control (sense) sequences. The extent of phenotypic changes are highly variable. Phenotypic effects induced by antisense are based on changes in criteria such as biological endpoints, protein levels, protein activation measurement and target mRNA levels.

D. Pharmaceutical Compositions

The above described substances including nucleic acids encoding EPM2B and mutated EPM2B, malin and mutated malin proteins, antibodies, and antisense oligonucleotides as well as other agents that modulate EPM2B/malin and/or mutated EPM2B/malin may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals.

Administration of a therapeutically active amount of pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of the substance to elicit a desired response in the individual. Dosage regimes may be adjusted to provide the optimum therapeutic response. For example, several divided doses may be administered daily or the dose may be proportionally reduced as indicated by the exigencies of the therapeutic situation.

An active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions which may inactivate the compound. If the active substance is a nucleic acid encoding, for example, a modified EPM2B gene may be delivered using techniques known in the art.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985) or Handbook of Pharmaceutical Additives (compiled by Michael and Irene Ash, Gower Publishing Limited, Aldershot, England (1995)). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456. As will also be appreciated by those skilled, administration of substances described herein may be by an inactive viral carrier.

E. Experimental Models

The present invention also includes methods and experimental models for studying the function of the EPM2B gene and malin protein. Cells, tissues and non-human animals that lack the EPM2B gene or partially lack in malin expression may be developed using recombinant expression vectors having a specific deletion or mutation in the EPM2B gene. A recombinant expression vector may be used to inactivate or alter the EPM2B gene by homologous recombination and thereby create an EPM2B deficient cell, tissue or animal.

Null alleles may be generated in cells, such as embryonic stem cells by deletion mutation. A recombinant EPM2B gene may also be engineered to contain an insertion mutation which inactivates EPM2B. Such a construct may then be introduced into a cell, such as an embryonic stem cell, by a technique such as transfection, electroporation, injection etc. Cells lacking an intact EPM2B gene may then be identified, for example by Southern blotting, Northern Blotting or by assaying for EPM2B using the methods described herein. Such cells may then be fused to embryonic stem cells to generate transgenic non-human animals deficient in EPM2B. Germline transmission of the mutation may be achieved, for example, by aggregating the embryonic stem cells with early stage embryos, such as 8 cell embryos, in vitro; transferring the resulting blastocysts into recipient females and; generating germline transmission of the resulting aggregation chimeras. Such a mutant animal may be used to define specific cell populations, developmental patterns and in vivo processes, normally dependent on EPM2B expression. The present invention also includes the preparation of tissue specific knock-outs of the EPM2B gene.

The following non-limiting example is illustrative of the present invention:

EXAMPLES

Example 1

The inventors examined all available databases and found 7 annotated genes in the newly defined critical region on chromosome 6p22.3 (FIG. 1). Based on their predicted functional characteristics each gene was prioritized for mutation screening through DNA sequencing of LD patients carrying an EPM2B haplotype, but no pathogenic variants were identified. Simultaneously, the inventors' analysis led to the discovery of a previously uncharacterized apparently single-exon (1188 bp) gene sharing extensive sequence identity with orthologous units (with equivalent protein-coding potential) in other higher vertebrates (75%, 78%, 87% nucleotide identity with rat, mouse, and dog, respectively). The human gene, designated as EPM2B, also had at its 5'-end all of the proposed features of the consensus sequence of an eukaryotic translational initiation site and, at its 3'-end, two putative polyadenylation signals (FIG. 1). Moreover, expressed sequence tag (EST) and cDNA data in human and mouse supported that the single-exon unit was a bona fide gene.

EPM2B would be predicted to encode a 395 amino acid (aa) protein that the inventors have named malin (mal for seizure in French) containing a zinc finger of the RING type in the N-terminal half and 6 NHL-repeat domains in the C-terminal direction (FIG. 1). Specifically, the zinc-binding RING-finger motif ($C-X_2-C-X_{16}-C-X_1-H-X_2-C-X_2-C-X_{14}-C-X_2-C$) was identified (E-value of 0.0067) between residues 26-71 of malin consistent with the signature sequence ($C-X_2-C-X_{9-39}-C-X_{1-13}-H-X_{2-3}-H-X_2-C-X_{4-48}-C-X_2-C$) of the RING-HC type (16,17). The presence of a RING finger is predictive of an E3 ubiquitin ligase function (8,9,18). E3 ligation is the final and specific step of the ubiquitin pathway transferring ubiquitin from E2, either directly or through adaptor proteins, to a specific substrate(s) to initiate its removal by the proteasome system (8). The 6 NHL domains (10-13) were predicted on the basis of presence of an approximately 44-residue motif rich in glycine and hydrophobic amino acids seeded with a cluster of charged residues (Pfam detected six trusted matches for NHL domains with E-values ranging from 0.011 to 3.5) (FIG. 1).

Northern-blot analysis indicated EPM2B is present (as at least two transcripts 1.5 kb and 2.4 kb in size) in all tissues examined including specific sub-regions of the brain (FIG. 3). The observed transcript sizes correspond near to the lengths expected between the predicted ATG-start site and the two different polyadenylation signals (FIG. 1). Moreover, the expression profile was similar to that observed for EPM2A, both being present in all tissues in which Lafora bodies have been observed (2,19).

The complete coding region of EPM2B was sequenced in a cohort of 34 LD probands previously shown not to carry mutations in EPM2A. In this Example, 17 different DNA sequence alterations are described in EPM2B in 26 families including 8 deletions and 1 insertion leading to frame-shifts, 7 missense, and 1 non-sense change (Table 1). These mutations were found in families in both homozygous (18) and compound heterozygous (8) recessive states. The four consanguineous F-C families used in the original linkage study all carried a homozygous 76T→A change producing a cysteine-to-serine alteration in one of the 7 conserved cysteine residues that are critical for the zinc-binding ability of the RING-finger domain (FIG. 2b). The most common mutation identified (7 families) was a homozygous 205C→G transition resulting in a proline to alanine change in the RING-finger domain. The LD38324 family that was critical in refining the EPM2B locus (FIG. 2a) carried a homozygous 2-bp deletion (1048-1049delGA) leading to a frame-shift mutation in the fifth NHL-domain (FIG. 2b). Referring to Table 1, in family LD51, DNA from the proband was not available but the parents were both heterozygous carriers of 468-469delAG, which would be predicted to lead to homozygous frame-shift mutations in the LD child. All of the mutations detected would affect the putative RING or NHL motifs, or would be predicted to lead to a frame-shift or cause drastic structural change in the protein (LD483 carries a 260T→C nucleotide change which would lead to a leucine to proline alteration). Four silent DNA sequence-coding variants were identified. Three of them T312C (H104H), G372C (G124G) and T1020C (G340G) were present in five, two, and one of 100 control chromosomes, respectively. The most common polymorphism detected, C332T (P111L) (FIG. 1) was observed on 42 of 100 control chromosomes.

In total, 88% or the LD families can now be accounted for by mutations in EPM2A (48%) and EPM2B (40%). The observation of 8 families with no detectable mutations in either of these genes suggests there could be additional LD loci.

Among other conditions with polyglucosan accumulation, including adult polyglucosan body disease (APBD) (20), LD is unique for the sub-cellular location of inclusions in neuronal dendrites but not axons (21), as is show in FIG. 4. The physical association of the forming polyglucosan fibrils with ER is also specific to LD (3). In APBD, which is caused by mutations in the glycogen branching enzyme (20,22,23), polyglucosans are indistinguishable in size, composition, and number from Lafora bodies, but they are located exclusively in the cell soma and axons (20). The presence of a seizure phenotype in LD but not in APBD implicates ER-associated dendritic accumulations of polyglucosans in the epilepsy of LD.

To examine the cellular localization of malin the inventors transfected an epitope-tagged EPM2B construct and found that it did indeed localize at the ER and to a lesser extent within the nucleus of cultured cells (FIG. 5). These results were similar to the cellular localization observed for the two alternative transcripts (A and B) of EPM2A, which encode isoforms of laforin found in the cytoplasm at the ER (24-26) (FIG. 4b) and in the nucleus, respectively (27). The inventors most recent data implicate loss of function of the cytoplasmic form of laforin in LD based on the identification of transcript A-specific mutations (L. I. et al., manuscript submitted). Moreover, the study of murine-EPM2A knockouts (28) and LD patients (1,2) has shown that the ER-associated polyglucosan bodies precede or are concomitant, respectively, with onset of epilepsy.

Therefore, in the simplest explanation, LD arises due to improper clearance, and subsequent accumulation of polyglucosans in dendrites, disturbing neuronal synaptic function leading to epileptogenesis. The inventors have now shown in transgenic LD mice that laforin contacts polyglucosans (and not glycogen) providing the first physical link between a disease gene product and LD pathology (E. M. C. et al., in preparation). Laforin's only other experimentally-validated function is that of a dual-specificity phosphatase (24,25), which would predict that there is at least one phosphoprotein intermediary through which it acts. Possible candidates could be the newly discovered EPM2AIP1 laforin-interacting protein (26), or other still to be cloned LD gene(s), or any of their interacting proteins. Malin will likely be involved via specific protein-protein interaction through its NHL domains followed by ubiquitin-mediated removal of a regulatory target(s), contributing a crucial role with laforin to safeguard neurons against Lafora bodies and epilepsy.

Methods

Samples

All patients described in this study were formally diagnosed with adolescent-onset progressive myoclonus epilepsy based on presence of pathognomonic Lafora bodies in biopsies of skin, skeletal muscle, liver or brain. Each LD individual and their family members (if available) were examined for involvement of the EPM2A locus at 6q24 by homozygosity mapping, mutation screening, or both.

Genotyping and Mutation Screening

Information and amplification conditions on the established (D6S274, D6S285, D6S966, D6S1567, D6S1678, D6S1688, D6S1959) and new (BV012563, BV012730, BV012565, BV012566, BV012568) are found in the UniSTS and Entrez Nucleotides database (http:/www.ncbi.nim.nih.gov/). DNA Sequence variations were detected by sequencing of PCR-products. To screen EPM2B, two sets of primer pairs that amplify overlapping fragments were used EPM2B-1F: (5'-ACTGTGACCGTGACCGAGA-3') (SEQ ID NO: 53) and EPM2B-1R: (CACACCCCAAGGTAAGGAGA-3') (SEQ ID NO: 54); EPM2B-2F: (5'-GACTGCCATGTGGT-TGTCAC-3') (SEQ ID NO: 55) and EPM2B-2R: (5'-AAA-CAATTCATTMTGGCAGCA-3') (SEQ ID NO: 56) (see FIG. 1). PCR was performed on 50 ng of DNA in buffer [75 mM Tris-HCl (pH 8.8), 20 mM (NH4)2SO4, 0.01% Tween 20, 1.5 mM MgC12, 1M Betaine, 0.2 mM dNTP, 0.2 µM of each primer, 2.5 Units of Taq Polymerase (MBI Fermentas)]. Cycling conditions were: initial denaturation at 94° C. for 3 min followed by 35 cycles of denaturation at 94° C. for 30 sec, annealing at 60° C. for 30 sec and extension at 72° C. for 30 sec, with a 10 min final extension at 72° C. PCR products were purified using mircroCLEAN (Microzone Ltd). 3 µl (100 ng/µl) of purified PCR product was used as sequencing template. For all reactions, 1 µl (5 pmol) of primer, 1.5 µl 5× sequencing buffer (Applied Biosystems), 1 µl BigDye Terminator v3.1, and 7.5 µl H2O in a 14 µl reaction volume were used. Thermocycling (MJ Research, Inc.) conditions were denaturing at 96° C. for 30 s; annealing at 50° for 20 s; and extension at 60° C. for 4 min; 35 cycles. All reactions were subsequently purified using multiscreen-HV filter plates (Millipore) and analyzed using an ABI-3700. All sequence variants detected in LD patients were examined in a collection of 50 (100 chromosomes) randomly selected DNA samples.

Gene Identification and Northern Blots

Gene annotation data and EST sequences were mainly obtained from the University of California Santa Cruz (UCSC) genome browser (http://genome.ucsc.edu/) and Celera Genomics (http://www.celera.com/). Additional putative genes were annotated using the Genescript algorithm (http://tcag.bioinfo.sickkids.on.ca/genescript/) and multi-species VISTA (http://www-gsd.lbl.gov/vista/) alignments between human and mouse sequence. The RING finger domain was predicted by Pfam, Prosite, InterProScan, SMART and MotifScan. NHL domains were identified using Pfam and InterProScan. EPM2B orthologues were identified using BLASTN and BLASTP analyses against the GenBank non-redundant database. Prediction of the sub-cellular localization of malin by sequence analysis was performed using PSORT II. No significant signal peptide sequence (for recognition of ER, Golgi complex, lysosome and integral plasma membrane proteins), mitbchondriail targeting sequence, nuclear localization signal and peroxisomal targeting signal was identified. The human multiple-tissue blot I and human brain blot II (Clontech) were probed with a [$^{32}$P]dCTP-labeled probe that was generated using the primers 5'-GTCAC-CATCACCMCGACTG-3' (SEQ ID NO: 57) and 5'-TGC-GAAAGACCATGAGTGAC-3' (SEQ ID NO: 58), which amplified a 557 by fragment within the coding region of EPM2B. Hybridization and washing conditions were performed according to the manufacturer's instructions.

Sub-Cellular Localization and Electron Microscopy

The myc-tagged EPM2A transcript A expression construct (pcDNA3mycEPM2A), which encodes the cytoplasmic isoform of laforin has been described (24). A myc-tagged EPM2B construct was generated (pcDNA3mycEPM2B) using the same general protocols. Full-length EPM2B was amplified by PCR from genomic DNA using the (forward) primer (5'-gqatccATGgcggccgaagc-3') (SEQ ID NO: 59) containing a BamHl restriction site (underlined) and the start codon (uppercase) and a (reverse) primer (5'-gcgqccqcacaat-tcaftaatggcagac-3') (SEQ ID NO: 60) (SEQ ID NO: 60) containing a NotI site (underlined). This product was cloned into the corresponding sites of the mammalian expression vector pcDNA3 (Invitrogen). Myc was then introduced, in frame, after amplifying from a previous myc-containing vector with 5' KpnI-tagged and 3' BamHI-tagged primers. pcDNA3mycEPM2A and pcDNA3mycEPM2B (2 mg) were transfected into Cos-7 cells using Lipofectamine-Plus (Invitrogen) and exposed to lipid-DNA complex in DMEM (Sigma-Aldrich) for 5 hours. Forty-eight hours post-transfection, cultures were rinsed twice in PBS and fixed for 15 min at −20.degree. C. in an acetone:methanol (1:1) mix. They were then stained with antibodies against myc-laforin and ER marker GRP94. Cultures were blocked for 1 hour (10% BSA/PBS) and incubated with anti-Myc and anti-ER for 45 min at room temperature. Slides were washed with PBS and incubated with secondary antibody (FITC-labeled goat anti-mouse, 1:400, detectable through the green filter; Texas red-labeled donkey anti-goat, 1:400, detectable through the red filter; Jackson ImmunoResearch Laboratories) in blocking solution. Following mounting (Dako Anti-Fade), they were analyzed by immunofluorescence light microscopy. For electron microscopic examination biopsy material was obtained from the LD patient and placed into chilled Universal fixative. Using standard protocols it was then analyzed at the ultrastructural level.

Example 2

In addition to the mutations described in Example 1, the inventors have found an additional 4 mutations in EPM2B that is associated with Lafora's disease. These mutations were described in the same fashion as Example 1. The DNA was obtained from blood from patients with Lafora disease clinically similar to the ones described in Example 1. The three mutations in EPM2B are as follows: 1) A deletion of nucleotide T at position 606; 2) An A to T change at nucleotide 923; 3) A G to T change at nucleotide 580; and 4) A G to T change at nucleotide 199. The latter mutation was found in both a Sudanese and Italian family. The additional mutations are listed at the bottom of Table 1.

Example 3

Lafora's disease has also been discovered in dogs with surprising frequency. Progressive myoclonus epilepsy (PME), is common (~5%) in the popular Miniature Wirehaired Dachshund (MWHD) breed in the United Kingdom. The inventors characterized the clinicopathologic phenotype of these dogs and show them to have LD. The inventors mapped the underlying disease locus and identified the specific disease-associated mutation (in the EPM2B gene): the first coding dodecamer repeat expansion in any species and the first disease-causing tandem repeat expansion outside human. The inventors have shown that the expansion mutation is recurrent, affecting epileptic dogs other than MWHD and demonstrate that it arises from a sequence variation particular to dogs (and other canids), predisposing the species to LD. Finally, the inventors devised a test to detect expanded alleles in carrier and presymptomatic animals and allow eradication of the disease from MWHD and future affected canine populations.

Fourteen affected MWHD with age of onset between six to nine years were initially evaluated. Myoclonus consisted of symmetrical split-second contractions of neck and limb muscles causing, retropulsion of the dog; jaws would chatter or snap shut, and eyelids would blink rapidly. Myoclonus occurred spontaneously but could be triggered by sudden noises, or visual stimuli such as a ball rolling towards the dog or the strobe of light through trees during a car ride. Myoclonus was less likely when the dog was focused such as during chasing after rabbits and more likely with excitement or nervousness such as at feeding time or with visitors. Atonic attacks causing the animal to suddenly sit or fall and generalized seizures with rigidity, paddling, vocalization, foaming at the mouth, urination and unconsciousness were common. Older dogs were ataxic and blind, their seizures more frequent and unresponsive to medications. Eventually (ages 9 to 12), myoclonus and drop attacks were constant, compelling euthanasia. This clinical picture precisely recapitulates human LD (2), as does the underlying pathology (FIG. 8).

Having confirmed that the dogs have LD, the inventors first cloned the canine EPM2A gene, and excluded its involvement. The inventors next undertook a genome-wide scan to localize the disease locus. The inventors genotyped 241 canine-specific microsatellite markers (31) spanning the entire canine genome in the 14 affected dogs and four unaffected relatives. The two markers at which the largest number of affected dogs were homozygous and the largest number of unaffected dogs heterozygous were REN94K23 and REN01G01, which map to the small 38 Mb chromosome 35 (CFA35). The inventors ascertained more dogs from the extended pedigree shown in FIG. 9a, and genotyped additional markers on CFA35. A maximum two-point LOD score of 2.65 at a recombination fraction θ=0.00 was obtained for marker REN157J09. Multipoint linkage analysis generated a maximum LOD score of 3.38 across five markers including REN157J09 (surpassing the significance threshold of 3.2 for canine linkage studies (32) (FIG. 9B), thereby linking MWHD LD to this region of CFA35.

As discussed in Example 1, the inventors mapped the human EPM2B locus to chromosomal band 6p22 (15). Canine CFA35 is syntenic, in its entirety, to human 6p21.33-6p25.2 (31), and it was therefore possible that the same gene is mutated in human EPM2B patients and MWHD LD cases. The inventors cloned human EPM2B first (33), used its single exon to probe the RPCI-81 canine bacterial artificial chromosome (BAC) library and isolated BAC 328A12, which upon sequencing using human EPM2B primers revealed the complete open reading frame of canine EPM2B (AY560905). Radiation hybrid mapping linked EPM2B to marker REN157J09 (LOD score 19.3), the same marker to which MWHD LD had linked (above) with maximum LOD score (FIG. 9b). In aggregate, these data argued that EPM2B was a viable candidate for the MWHD disease.

PCR amplification of the canine EPM2B gene initially failed in affected but not unaffected MWHD across a region in the 5' half of the gene. Examination of the normal sequence in this region revealed two consecutive identical dodecamers, and a third copy differing by a single nucleotide (the perfectly repeated copy is termed D and the third imperfect copy T, for ease of reference) (FIG. 10a). The corresponding region in other sequenced species (FIG. 10a) is not repetitive and the canine sequence is longer by 12 nucleotides, the length of one D repeat (FIG. 10a). Concerted modifications of PCR conditions to amplify and sequence across this region in affected animals ultimately succeeded and revealed the MWHD LD mutation: all affected animals had bi-allelic expansions of the dodecamer repeat, with 19 to 26 copies of the D sequence in each allele (FIGS. 9a, 10b). The expansions are in-frame and might permit protein, albeit abnormal, to be made if mRNA containing them are stable.

The inventors next tested the effect of the expansion mutation on mRNA stability by comparing the amount of EPM2B mRNA in skeletal muscle from three affected dogs and two controls using quantitative RT-PCR (Supplementary Methods). EPM2B mRNA levels were more than 900 times reduced in the affected animals (FIG. 10c).

The extra D sequence characterizing canine EPM2B was initially detected in the BAC, of Doberman Pinscher origin, and in the normal MWHD. The inventors considered whether this is a feature of only some breeds of dog, predisposing them, at least in the case of the MWHD, to expansion and LD. The inventors sequenced EPM2B from two normal unrelated dogs from each of 128 different breeds. Sixty percent of chromosomes had three repeats and 40% two repeats. Alleles with three repeats consisted always of two D's and one T and those with two repeats of one D and one T. Almost all breeds had examples of both variants, in homozygous or heterozygous state. Inheritance, tested in three four-generation families of different breeds, was Mendelian.

Having shown that the dodecamer repeat is present across the canine species, the inventors considered whether its expansion is a cause of myoclonic seizures in other breeds of dog. The inventors tested the next non-MWHD PME case to present to the clinic, a Bassett Hound, and found a homozygous seven-fold expansion (14 copies) of the D repeats (FIG. 10b).

The sequence of the dodecamer expansion mutation is composed exclusively of G and C nucleotides. In the presence of the normal allele, PCR of the expanded allele was impossible, and hence carriers could not be determined. To detect carriers, the inventors deaminated the DNA, converting unmethylated cytosines to uracils, and then PCR-amplified, which allowed amplification of the mutant allele, and reliable detection of carrier MWHD (FIG. 3b). Deamination also greatly facilitated PCR amplification and diagnosis of affected animals.

The deamination method employed above was originally developed (34) for the amplification of an until now unique dodecamer repeat expansion mutation arising from a two to three-copy dodecamer repeat sequence specific to the human cystatin-B gene promoter and causing EPM1, another form of PME, by impeding cystatin-B expression (35). In humans, the more than 60 mutations in the two LD genes (EPM2A and EPM2B) (http://projects.tcag.ca/lafora/) are not the most common cause of PME. Instead, the single, recurring, cystatin-B promoter expansion mutation causes most human PME. To the inventors' knowledge, EPM1 has never been described in dogs, likely because they do not have the cystatin-B dodecamer repeat. LD, on the other hand is regularly reported in dogs (Basset Hounds (36,37,38), Miniature (36) and Standard (39) Poodles, Pointers (40), Corgis (41), Beagles (42, 43,44) and MWHD (45,46). This is likely due to recurrent expansion events of the EPM2B repeat, combined with the intensive inbreeding so prevalent in the domesticated dog. In other domesticated animals LD is exceedingly rare: two cows identified during mass testing for bovine spongiform encephalopathy (47) (which clinically resembles LD) and one cat (48).

Presence of the dodecamer repeat across canine breed barriers (49) suggests that its origin predates dogs and that it might therefore be present in related species. The inventors determined the distribution of the repeat in the order Carnivora and show that it is specific to the Canidae family (wolves, dogs, foxes, coyotes and jackals) (FIG. 10d). The inventors were also able to discern the repeat's evolution, which occurred in two steps: appearance of the D sequence and then its duplication. Carnivores separated into Felidae and Canoidae in the Paleocene ~60 million years ago (Ma) (50,51). The D sequence is present across extant Canoidae but not Felidae (FIG. 10d). It therefore first appeared after the feline-canoid split and before the subsequent divergence of canoids into Arctoidae and Canidae ~50 Ma (FIG. 10d). Arctoids flourished on the Eurasian continent where they evolved into extant bears, skunks, racoons, otters, etc. (50). These species have a single copy of the D sequence (FIG. 10d). Canids occupied the equivalent niches on the North American landmass (successfully defending it against arctoid incursions for 40 million years) (50), and evolved by ~10 Ma to present-day wolves, dogs, foxes, coyotes and jackals (51), all of which have the duplicated D sequence (FIG. 10d). Duplication of the D sequence therefore occurred in the canid evolutionary line, sometime between 50 Ma and 10 Ma. Whether the resulting variable four-amino acid lengthening of the middle portion of main (FIG. 10a) confers a property to this E3 ligase advantageous to canids remains to be seen.

Epilepsy is the most common neurological disorder of dogs. Its prevalence is at least five times higher than in human (52). Here, the inventors have discovered the first canine epilepsy mutation. To what extent it contributes to other forms of canine epilepsy remains to be determined.

In the United Kingdom, LD is presently widespread in the MWHD, a breed with ~800 dogs registered each year. Through popular carrier sires and repeatedly bred carrier champions the disease has spread to South Africa and North America (data not shown). In the United States, different dachshund coat types are considered varieties of the same breed and are intercrossed, which might spread the disease throughout the dachshund. The mutation detection test resulting from the work described here should instead allow its eradication through controlled breeding. Meanwhile, these animals are loved pets and receive neurologic care. They far outnumber human LD patients followed in any one medical centre. This is affording the inventors important experience with best treatments for this disease, which the inventors are applying to human patients.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

EPM2B mutations identified in LD patients.

| Family | Origin | Nucleotide change | Predicted Effect |
| --- | --- | --- | --- |
| LD6 | F-Canada | Homozygous 76T→A | C26S (missense RING finger) |
| LD7 | F-Canada | Homozygous 76T→A | C26S (missense RING finger) |

TABLE 1-continued

EPM2B mutations identified in LD patients.

| Family | Origin | Nucleotide change | Predicted Effect |
|---|---|---|---|
| LD27 | F-Canada | Homozygous 76T→A | C26S (missense RING finger) |
| LD28 | F-Canada | Homozygous 76T→A | C26S (missense RING finger) |
| LD23102 | Brazil | Homozygous 205C→G | P69A (missense RING finger) |
| LDlaf100 | Brazil | Homozygous 205C→G | P69A (missense RING finger) |
| LD5922 | Italy | Homozygous 205C→G | P69A (missense RING finger) |
| LDlaf26 | Italy | Heterozygous 205C→G 838G→A | P69A (missense RING finger) E279K (missense NHL 4) |
| LD41818 | Spain | Heterozygous 205C→G 468delA | P69A (missense RING finger) G158fs173 (frameshift) |
| LD35180 | F-Canada | Heterozygous 205C→G 204delC | P69A (missense RING finger) P69fs21 (frameshift RING finger) |
| LD29852 | United States | Heterozygous 205C→G 468–469delAG | P69A (missense RING finger) G158fs16 (frameshift) |
| LD34477 | India | Heterozygous 468–469delAG 676C→T | G158fs16 (frameshift) Q226X (nonsense NHL 3) |
| LD51 | Brazil | Homozygous 468–469delAG | G158fs16 (frameshift) |
| LDlaf101 | Italy | Homozygous 468–469delAG | G158fs16 (frameshift) |
| LDlaf9 | Yugoslavia | Heterozygous 992delG 468–469delAG | G321fs2 (frameshift NHL 5) G158fs16 (frameshift) |
| LDlaf1 | Yugoslavia | Heterozygous 992delG 468–469delAG | G321fs2 (frameshift NHL 5) G158fs16 (frameshift) |
| LD949 | Bosnia | Homozygous 992delG | G321fs2 (frameshift NHL 5) |
| LD38324 | Yugoslavia | Homozygous 1048–1049delGA | E340fs40 (frameshift NHL 5) |
| LD7635 | Israel | Homozygous 373–382del10bp | T125fs103 (frameshift) |
| LD628 | Italy | Homozygous 661–692del32bp | V16fs1 (frameshift NHL 3) |
| LD483 | Italy | Homozygous 260T→C | L87P (missense) |
| LD22830 | Canada | Homozygous 905A→C | Q29P (missense NHL 4) |
| LD32817 | Pakistan | Homozygous 98T→C | F33S (missense RING finger) |
| LD25-9 | Saudi Arabia | Homozygous 892ins2T | S298fs15 (frameshift NHL 4) |
| LD5487 | Denmark | Heterozygous 436G→A 1100delT | D146N (missense NHL 1) V362fs20 (frameshift) |
| LD5489 | Denmark | Homozygous 1100delT | V362fs20 (frameshift) |
| Laf25 | Italian | 606delT Homozygous | F204fs27 |
| Laf41 | Italian | 923A→T Homozygous | D308V |
| 3422 | Sudanese | 580G→T Homozygous | G194C |
| Laf44 | Italian | 199G→T Homozygous | E67X |

FULL CITATIONS FOR REFERENCES REFERRED TO IN THE SPECIFICATION

1. Lafora, G. R., Gluck, B. Beitrag zur histopathologie der myoklonischen epilepsie. Z Ges Neurol Psychiat 6, 1-14 (1911).
2. Minassian, B. A. Progressive myoclonus epilepsy with polyglucosan bodies: Lafora disease. Adv Neurol 89, 199-210 (2002).
3. Collins, G. H., Cowden, R. R. & Nevis, A. H. Myoclonus epilepsy with Lafora bodies. An ultrastructural and cytochemical study. Arch Pathol 86, 239-54 (1968).
4. Sakai, M., Austin, J., Witmer, F. & Trueb, L. Studies in myoclonus epilepsy (Lafora body form). II. Polyglucosans in the systemic deposits of myoclonus epilepsy and in corpora amylacea. Neurology 20, 160-76 (1970).
5. Minassian, B. A. et al. Genetic locus heterogeneity in Lafora's progressive myoclonus epilepsy. Ann Neurol 45, 262-5 (1999).
6. Minassian, B. A. et al. Mutations in a gene encoding a novel protein tyrosine phosphatase cause progressive myoclonus epilepsy. Nat Genet 20, 171-4 (1998).
7. Minassian, B. A. et al. Mutation spectrum and predicted function of laforin in Lafora's progressive myoclonus epilepsy. Neurology 55, 341-6 (2000).
8. Jackson, P. K. et al. The lore of the RINGs: substrate recognition and catalysis by ubiquitin ligases. Trends Cell Biol 10, 429-39 (2000).
9. Hatakeyama, S. & Nakayama, K. I. U-box proteins as a new family of ubiquitin ligases. Biochem Biophys Res Commun 302, 635-45 (2003).
10. Fridell, R. A., Harding, L. S., Bogerd, H. P. & Cullen, B. R. Identification of a novel human zinc finger protein that specifically interacts with the activation domain of lentiviral Tat proteins. Virology 209, 347-57 (1995).
11. Frank, D. J. & Roth, M. B. ncl-1 is required for the regulation of cell size and ribosomal RNA synthesis in *Caenorhabditis elegans*. J Cell Biol 140, 1321-9 (1998).
12. Slack, F. J. & Ruvkun, G. A novel repeat domain that is often associated with RING finger and B-box motifs. Trends Biochem Sci 23, 474-5 (1998).
13. Slack, F. J. et al. The lin-41 RBCC gene acts in the *C. elegans* heterochronic pathway between the let-7 regulatory RNA and the LIN-29 transcription factor. Mol Cell 5, 659-69 (2000).
14. Serratosa, J. M. et al. A novel protein tyrosine phosphatase gene is mutated in progressive myoclonus epilepsy of the Lafora type (EPM2A). Hum Mol Genet 8, 345-52 (1999).
15. Chan, E. M. et al. Genetic mapping of a new Lafora Progressive Myoclonus Epilepsy locus (EPM2B) on 6p22. Journal of Medical Genetics, 40, 671-5 (2003).
16. Freemont, P. S. The RING finger. A novel protein sequence motif related to the zinc finger. Ann NY Acad Sci 684, 174-92 (1993).
17. Saurin, A. J., Borden, K. L., Boddy, M. N. & Freemont, P. S; Does this have a familiar RING? Trends Biochem Sci 21, 208-14 (1996).

18. Freemont, P. S. RING for destruction? Curr Biol 10, R84-7 (2000).
19. Schwarz, G. A. & Yanoff, M. Lafora disease, distinct clinico-pathological form of Unverricht's syndrome. Arch Neurol 12, 172-188 (1965).
20. Robitaille, Y., Carpenter, S., Karpati, G. & DiMauro, S. D. A distinct form of adult polyglucosan body disease with massive involvement of central and peripheral neuronal processes and astrocytes: a report of four cases and a review of the occurrence of polyglucosan bodies in other conditions such as Lafora's disease and normal ageing. Brain 103, 315-36 (1980).
21. Cavanagh, J. B. Corpora-amylacea and the family of polyglucosan diseases. Brain Res Brain Res Rev 29, 265-95 (1999).
22. Thon, V. J., Khalil, M. & Cannon, J. F. Isolation of human glycogen branching enzyme cDNAs by screening complementation in yeast. J Biol Chem 268, 7509-13 (1993).
23. Lossos, A. et al. Adult polyglucosan body disease in Ashkenazi Jewish patients carrying the Tyr329Ser mutation in the glycogen-branching enzyme gene. Ann Neurol 44, 867-72 (1998).
24. Minassian, B. A. et al. Laforin is a cell membrane and endoplasmic reticulum-associated protein tyrosine phosphatase. Ann Neurol 49, 271-5 (2001).
25. Ganesh, S. et al. Laforin, defective in the progressive myoclonus epilepsy of Lafora type, is a dual-specificity phosphatase associated with polyribosomes. Hum Mol Genet 9, 2251-61 (2000).
26. Ianzano, L., Zhao, X. C., Minassian, B. A., Scherer, S. W. Identification of a novel protein interacting with laforin, the EPM2A Progressive Myoclonus Epilepsy gene product. Genomics 81, 579-587 (2003).
27. Ganesh, S., Suzuki, T. & Yamakawa, K. Alternative splicing modulates subcellular localization of laforin. Biochem Biophys Res Commun 291, 1134-7 (2002).
28. Ganesh, S. et al. Targeted disruption of the Epm2a gene causes formation of Lafora inclusion bodies, neurodegeneration, ataxia, myoclonus epilepsy and impaired behavioral response in mice. Hum Mol Genet 11, 1251-62 (2002).
29. Kozak, M. Interpreting cDNA sequences: some insights from studies on translation. Mamm Genome 7, 563-74 (1996).
30. Lovering, R. et al. Identification and preliminary characterization of a protein motif related to the zinc finger. Proc Natl Acad Sci USA 90, 2112-6 (1993).
31. Guyon, R. et al. A 1-Mb resolution radiation hybrid map of the canine genome. Proc Natl Acad Sci USA 100, 5296-301 (2003).
32. Gordon, D., Corwin, M. B., Mellersh, C. S., Ostrander, E. A. & Ott, J. Establishing appropriate genome-wide significance levels for canine linkage analyses. J Hered 94, 1-7 (2003).
33. Chan, E. M. et al. Mutations in NHLRC1 cause progressive myoclonus epilepsy. Nat Genet 35, 125-7 (2003).
34. Weinhaeusel, A., Morris, M. A., Antonarakis, S. E. & Haas, O. A. DNA deamination enables direct PCR amplification of the cystatin B (CSTB) gene-associated dodecamer repeat expansion in myoclonus epilepsy type Unverricht-Lundborg. Hum Mutat 22, 404-8 (2003).
35. Lalioti, M. D. et al. Dodecamer repeat expansion in cystatin B gene in progressive myoclonus epilepsy. Nature 386, 847-51 (1997).
36. Holland, J. M., Davis, W. C., Prieur, D. J. & Collins, G. H. Lafora's disease in the dog. A comparative study. Am J Pathol 58, 509-30 (1970).
37. Jian, Z., Alley, M. R., Cayzer, J. & Swinney, G. R. Lafora's disease in the dog. A comparative study. N Z Vet J 38, 75-79 (1990).
38. Kaiser, E., Krauser, K. & Schwartz-Porsche, D. [Lafora disease (progressive myoclonic epilepsy) in the Bassett hound-possibility of early diagnosis using muscle biopsy?]. Tierarztl Prax 19, 290-5 (1991).
39. Cusick, P. K., Cameron, A. M. & Parker, A. J. Canine neuronal glycoproteinosis-Lafora's disease in the dog. J Am Anim Hosp Assoc 12, 518-521 (1976).
40. Mackenzie, C. D. & Johnson, R. P. Lafora's disease in a dog. Aust Vet J 52, 144 (1976).
41. Davis, K. E., Finnie, J. W. & Hooper, P. T. Lafora's disease in a dog. Aust Vet J 67, 192-3 (1990).
42. Hegreberg, G. A. & Padgett, G. A. Inherited progressive epilepsy of the dog with comparisons to Lafora's disease of man. Fed Proc 35, 1202-5 (1976).
43. Montgomery, D. L. & Lee, A. C. Brain damage in the epileptic beagle dog. Vet Pathol 20, 160-9 (1983).
44. Gredal, H., Berendt, M. & Leifsson, P. S. Progressive myoclonus epilepsy in a beagle. J Small Anim Pract 44, 511-4 (2003).
45. Fitzmaurice, S. & Shelton, G. D. 'Twitchiness' in miniature wirehaired dachshunds. Vet Rec 143, 204 (1998).
46. Schoeman, T., Williams, J. & van Wilpe, E. Polyglucosan storage disease in a dog resembling Lafora's disease. J Vet Intern Med 16, 201-7 (2002).
47. Simmons, M. M. Lafora disease in the cow? J Comp Pathol 110, 389-401 (1994).
48. Hall, D. G., Steffens, W. L. & Lassiter, L. Lafora bodies associated with neurologic signs in a cat. Vet Pathol 35, 218-20 (1998).
49. Parker, H. G. et al. Genetic structure of the purebred domestic dog. Science 304, 1160-4 (2004).
50. Janis, C. M., Scott, K. M. & Jacobs, L. L. Evolution of Tertiary mammals of North America (Cambridge University Press, Cambridge; N.Y., 1998).
51. Vila, C., Maldonado, J. E. & Wayne, R. K. Phylogenetic relationships, evolution, and genetic diversity of the domestic dog. J Hered 90, 71-7 (1999).
52. Licht, B. G. et al. Clinical presentations of naturally occurring canine seizures: similarities to human seizures. Epilepsy Behav 3, 460-470 (2002).

What is claimed is:

1. A method of detecting the presence of, or predisposition to, Lafora's disease in a human, wherein the Lafora's disease is associated with a mutation in the EPM2B gene, comprising detecting a C to G change at nucleotide number 205 in the EPM2B gene sequence comprising SEQ ID NO:1, wherein the presence of a C to G change at nucleotide number 205 in the EPM2B gene sequence comprising SEQ ID NO: 1 indicates the presence of, or predisposition to, Lafora's disease in the human.

2. The method of claim 1 further comprising detecting one or more mutations in said EPM2B gene selected from the group consisting of:
   (a) a T to A change at nucleotide number 76 in the EPM2B gene sequence comprising SEQ ID NO:1;
   (b) a deletion of nucleotides GA at nucleotide positions 1048 and 1049 in the EPM2B gene sequence comprising SEQ ID NO:1;
   (c) a deletion of nucleotides AG at nucleotide positions 468 and 469 in the EPM2B gene sequence comprising SEQ ID NO:1;
   (d) a deletion of nucleotide G at nucleotide number 992 in the EPM2B gene sequence comprising SEQ ID NO:1;
   (e) a deletion of 10 by at nucleotide positions 373 to 382 in the EPM2B gene sequence comprising SEQ ID NO:1;
   (f) a deletion of 32 by at nucleotide positions 661 to 692 in the EPM2B gene sequence comprising SEQ ID NO:1;
   (g) a T to C change at nucleotide number 260 in the EPM2B gene sequence comprising SEQ ID NO:1;
   (h) a A to C change at nucleotide number 905 in the EPM2B gene sequence comprising SEQ ID NO:1;
   (i) a T to C change at nucleotide number 98 in the EPM2B gene sequence comprising SEQ ID NO:1;
   (j) an insertion of 2 Ts at nucleotide number 892 in the EPM2B gene sequence comprising SEQ ID NO:1;
   (k) a G to A change at nucleotide number 436 in the EPM2B gene sequence comprising SEQ ID NO:1;
   (l) a deletion of nucleotide T at nucleotide number 1100 in the EPM2B gene sequence comprising SEQ ID NO:1;
   (m) a deletion of nucleotide T at nucleotide position 606 in the EPM2B gene sequence comprising SEQ ID NO:1;
   (n) a A to T change at nucleotide number 923 in the EPM2B gene sequence comprising SEQ ID NO:1;
   (o) a G to T change at nucleotide number 580 in the EPM2B gene sequence comprising SEQ ID NO:1;
   (p) a G to T change at nucleotide number 199 in the EPM2B gene sequence comprising SEQ ID NO:1;
   (q) a G to A change at nucleotide number 838 in the EPM2B gene sequence comprising SEQ ID NO:1;
   (r) a C to T change at nucleotide number 676 in the EPM2B gene sequence comprising SEQ ID NO:1;
   (s) a deletion of nucleotide A at nucleotide position 468 in the EPM2B gene sequence comprising SEQ ID NO:1; and (t) a deletion of nucleotide C at nucleotide position 204 in the EPM2B gene sequence comprising SEQ ID NO:1.

3. A method of detecting the presence or absence of a mutation in a nucleic acid in a test sample obtained from a human, wherein the test sample contains the EPM2B gene, the method comprising the steps of:
(a) analyzing the test sample containing the EPM2B gene to determine the nucleic acid sequence of the gene;
(b) comparing the nucleic acid sequence of the gene in the test sample to the nucleic acid sequence set forth in SEQ ID NO:1; and
(c) determining the differences, if any, between the sequence of the EPM2B gene in the test sample and the nucleic acid sequence set forth in SEQ ID NO:1, thereby detecting the presence or absence of a mutation in the EPM2B gene of the test sample.

4. The method of claim 3 wherein the test sample is amplified using suitable PCR primer sequences prior to analysis.

5. The method of claim 3 wherein the one or more mutations detected in said EPM2B gene are selected from the group consisting of:
(a) a C to G change at nucleotide number 205 in the EPM2B gene sequence comprising SEQ ID NO:1;
(b) a T to A change at nucleotide number 76 in the EPM2B gene sequence comprising SEQ ID NO:1;
(c) a deletion of nucleotides GA at nucleotide positions 1048 and 1049 in the EPM2B gene sequence comprising SEQ ID NO:1;
(d) a deletion of nucleotides AG at nucleotide positions 468 and 469 in the EPM2B gene sequence comprising SEQ ID NO:1;
(e) a deletion of nucleotide G at nucleotide number 992 in the EPM2B gene sequence comprising SEQ ID NO:1;
(f) a deletion of 10 by at nucleotide positions 373 to 382 in the EPM2B gene sequence comprising SEQ ID NO:1;
(g) a deletion of 32 by at nucleotide positions 661 to 692 in the EPM2B gene sequence comprising SEQ ID NO:1;
(h) a T to C change at nucleotide number 260 in the EPM2B gene sequence comprising SEQ ID NO:1;
(i) a A to C change at nucleotide number 905 in the EPM2B gene sequence comprising SEQ ID NO:1;
(j) a T to C change at nucleotide number 98 in the EPM2B gene sequence comprising SEQ ID NO:1;
(k) an insertion of 2 Ts at nucleotide number 892 in the EPM2B gene sequence comprising SEQ ID NO:1;
(l) a G to A change at nucleotide number 436 in the EPM2B gene sequence comprising SEQ ID NO:1;
(m) a deletion of nucleotide T at nucleotide number 1100 in the EPM2B gene sequence comprising SEQ ID NO:1;
(n) a deletion of nucleotide T at nucleotide position 606 in the EPM2B gene sequence comprising SEQ ID NO:1;
(o) a A to T change at nucleotide number 923 in the EPM2B gene sequence comprising SEQ ID NO:1;
(p) a G to T change at nucleotide number 580 in the EPM2B gene sequence comprising SEQ ID NO:1;
(q) a G to T change at nucleotide number 199 in the EPM2B gene sequence comprising SEQ ID NO:1;
(r) a G to A change at nucleotide number 838 in the EPM2B gene sequence comprising SEQ ID NO:1;
(s) a C to T change at nucleotide number 676 in the EPM2B gene sequence comprising SEQ ID NO:1;
(t) a deletion of nucleotide A at nucleotide position 468 in the EPM2B gene sequence comprising SEQ ID NO:1; and
(u) a deletion of nucleotide C at nucleotide position 204 in the EPM2B gene sequence comprising SEQ ID NO:1.

6. A method of detecting SEQ ID NO: 1 comprising
a) obtaining a test sample from a human,
b) hybridizing a probe consisting of SEQ ID NO: 1 with the test sample, and
c) detecting SEQ ID NO: 1 in the test sample.

7. A method of detecting the presence of, or predisposition to, Lafora's disease in a human, wherein the Lafora's disease is associated with a mutation in the EPM2B gene, comprising:
a) obtaining a nucleic acid sample which contains the EPM2B gene from the human;
b) sequencing the nucleic acids in the sample to detect a C to G change at nucleotide number 205 in the EPM2B gene sequence comprising SEQ ID NO:1; and
c) identifying the human as having Lafora's disease, or a predisposition to Lafora's disease, if the presence of a C to G change at nucleotide number 205 in the EPM2B gene sequence comprising SEQ ID NO: 1 is detected.

8. The method of claim 7 further comprising detecting one or more mutations in said EPM2B gene selected from the group consisting of:
(a) a T to A change at nucleotide number 76 in the EPM2B gene sequence comprising SEQ ID NO:1;
(b) a deletion of nucleotides GA at nucleotide positions 1048 and 1049 in the EPM2B gene sequence comprising SEQ ID NO:1;
(c) a deletion of nucleotides AG at nucleotide positions 468 and 469 in the EPM2B gene sequence comprising SEQ ID NO:1;
(d) a deletion of nucleotide G at nucleotide number 992 in the EPM2B gene sequence comprising SEQ ID NO:1;
(e) a deletion of 10 by at nucleotide positions 373 to 382 in the EPM2B gene sequence comprising SEQ ID NO:1;
(f) a deletion of 32 by at nucleotide positions 661 to 692 in the EPM2B gene sequence comprising SEQ ID NO:1;
(g) a T to C change at nucleotide number 260 in the EPM2B gene sequence comprising SEQ ID NO:1;
(h) a A to C change at nucleotide number 905 in the EPM2B gene sequence comprising SEQ ID NO:1;
(i) a T to C change at nucleotide number 98 in the EPM2B gene sequence comprising SEQ ID NO:1;
(j) an insertion of 2 Ts at nucleotide number 892 in the EPM2B gene sequence comprising SEQ ID NO:1;
(k) a G to A change at nucleotide number 436 in the EPM2B gene sequence comprising SEQ ID NO:1;
(l) a deletion of nucleotide T at nucleotide number 1100 in the EPM2B gene sequence comprising SEQ ID NO:1;
(m) a deletion of nucleotide T at nucleotide position 606 in the EPM2B gene sequence comprising SEQ ID NO:1;
(n) a A to T change at nucleotide number 923 in the EPM2B gene sequence comprising SEQ ID NO:1;
(o) a G to T change at nucleotide number 580 in the EPM2B gene sequence comprising SEQ ID NO:1;
(p) a G to T change at nucleotide number 199 in the EPM2B gene sequence comprising SEQ ID NO:1;
(q) a G to A change at nucleotide number 838 in the EPM2B gene sequence comprising SEQ ID NO:1;
(r) a C to T change at nucleotide number 676 in the EPM2B gene sequence comprising SEQ ID NO:1;
(s) a deletion of nucleotide A at nucleotide position 468 in the EPM2B gene sequence comprising SEQ ID NO:1; and
(t) a deletion of nucleotide C at nucleotide position 204 in the EPM2B gene sequence comprising SEQ ID NO:1.

* * * * *

UNITED STATES PATENT AND TRADEMARK OFFICE
CERTIFICATE OF CORRECTION

PATENT NO. : 7,871,768 B2  
APPLICATION NO. : 10/567074  
DATED : January 18, 2011  
INVENTOR(S) : Stephen W. Scherer and Berge A. Minassian Page 1 of 1

It is certified that error appears in the above-identified patent and that said Letters Patent is hereby corrected as shown below:

Column 63, Claim 2, line 64, delete "by" and insert -- bp --.

Column 63, Claim 2, line 66, delete "by" and insert -- bp --.

Column 65, Claim 5, line 34, delete "by" and insert -- bp --.

Column 65, Claim 5, line 36, delete "by" and insert -- bp --.

Column 66, Claim 8, line 32, delete "by" and insert -- bp --.

Column 63, Claim 8, line 34, delete "by" and insert -- bp --.

Signed and Sealed this  
Fifth Day of April, 2011

David J. Kappos  
*Director of the United States Patent and Trademark Office*

SEQUENCE LISTING

```
<160> NUMBER OF SEQ ID NOS: 60

<210> SEQ ID NO 1
<211> LENGTH: 2120
<212> TYPE: DNA
<213> ORGANISM: Homo sapiens

<400> SEQUENCE: 1
```

```
atggcggccg aagcctcgga gagcgggcca gcgctgcatg agctcatgcg cgaggcggag    60
atcagcctgc tcgagtgcaa ggtgtgcttt gagaagtttg gccaccggca gcagcggcgc   120
ccgcgcaacc tgtcctgcgg ccacgtggtc tgcctggcct gcgtggccgc cctggcgcac   180
ccgcgcactc tggccctcga gtgcccattc tgcaggcgag cttgccgggg ctgcgacacc   240
agcgactgcc tgccggtgct gcacctcata gagctcctgg gctcagcgct tcgccagtcc   300
ccggccgccc atcgcgccgc cccagcgcc cccggagccc tcacctgcca ccacccttc    360
ggcggctggg ggaccctggt caaccccacc ggactggcgc tttgtcccaa gacggggcgt   420
gtcgtggtgg tgcacgacgg caggaggcgt gtcaagattt ttgactcagg gggaggatgc   480
gcgcatcagt ttggagagaa gggggacgct gcccaagaca ttaggtaccc tgtggatgtc   540
accatcacca acgactgcca tgtggttgtc actgacgccg gcgatcgctc catcaaagtg   600
tttgattttt ttggccagat caagcttgtc attggaggcc aattctcctt accttggggt   660
gtggagacca cccctcagaa tgggattgtg gtaactgatg cggaggcagg gtccctgcac   720
ctcctggacg tcgacttcgc ggaagggggtc cttcggagaa ctgaaaggtt gcaagctcat   780
ctgtgcaatc cccaggggt ggcagtgtct tggctcaccg gggccattgc ggtcctggag    840
caccccctgg ccctggggac tggggttttgc agcaccaggg tgaaagtgtt tagctcaagt   900
atgcagcttg tcggccaagt ggatacctt gggctgagcc tctactttcc ctccaaaata    960
actgcctccg ctgtgacctt tgatcaccag ggaaatgtga ttgttgcaga tacatctggt  1020
ccagctatcc tttgcttagg aaaacctgag gagtttccag taccgaagcc catggtcact  1080
catggtcttt cgcatcctgt ggctcttacc ttcaccaagg agaattctct tcttgtgctg  1140
gacacagcat ctcattctat aaagtctat aaagttgact gggggtgatg ggctggggtg   1200
ggtccctgga atcagaagca ctagtgctgc cattaatgaa ttgtttaacc ctggataagt  1260
cacttaaact catctatcca ggcagggata attaaaacca tctggcagac ttacaaagct  1320
tgggacagtt attggagatt aatctaccat ttattgaatg catactctgt gcaaggaaat  1380
ttgcaaatat tagcttattt aatctgtact atccagtgag gtaatttctt cccccccaag  1440
atagagtcaa gctctgtcac ccaggctgga gtgcagaagc atgatcacag ctcactacag  1500
tttcaacgtc cccgctcag gtggtccttc cacctcagcc tcccaagtag ctgggaccac   1560
aagtgtgcat taccacactc agctaatttt tgtatttttgg cagagatggg gtttcaccat  1620
gttgcccagg ctggtctcaa actcctgagt tcaagcaatc caccttcctc ggcctcccaa  1680
agtactagga gtacaggcat agccacttgc tcagccataa tttttattat taatctcatt  1740
gtacaagtga gaaaactgag acccagagag cttaagtgac ttcctcgagg tcatagttac  1800
ttactgcctt agtcccaatt tgaattcaat tctgattcca aataagttgc gcttaaataa  1860
gacaacagat gtgggaaaaa tatgtgaatg tgtagtgttg ctatgtgtac tgtctttaca  1920
agtagctaat tattttagca caaagatgtg caaagaaagg agactttatg agagttcag   1980
gagaaaaagg atttttgtggt ggccatcact ttcattcaat ttgcgactgc tctgatggca  2040
cattagatga agttactgtt gatcctgagt tacgtgaata agaaaaacaa ttgaactgct  2100
tattaaaaaa gtaaacatgt                                              2120
```

<210> SEQ ID NO 2
<211> LENGTH: 395
<212> TYPE: PRT
<213> ORGANISM: Homo sapiens

<400> SEQUENCE: 2

```
Met Ala Ala Glu Ala Ser Glu Ser Gly Pro Ala Leu His Glu Leu Met
1               5                   10                  15

Arg Glu Ala Glu Ile Ser Leu Leu Glu Cys Lys Val Cys Phe Glu Lys
            20                  25                  30

Phe Gly His Arg Gln Gln Arg Pro Arg Asn Leu Ser Cys Gly His
        35                  40                  45

Val Val Cys Leu Ala Cys Val Ala Ala Leu Ala His Pro Arg Thr Leu
    50                  55                  60

Ala Leu Glu Cys Pro Phe Cys Arg Arg Ala Cys Arg Gly Cys Asp Thr
65                  70                  75                  80

Ser Asp Cys Leu Pro Val Leu His Leu Ile Glu Leu Leu Gly Ser Ala
                85                  90                  95

Leu Arg Gln Ser Pro Ala Ala His Arg Ala Ala Pro Ser Ala Pro Gly
            100                 105                 110

Ala Leu Thr Cys His His Thr Phe Gly Gly Trp Gly Thr Leu Val Asn
        115                 120                 125

Pro Thr Gly Leu Ala Leu Cys Pro Lys Thr Gly Arg Val Val Val Val
130                 135                 140

His Asp Gly Arg Arg Val Lys Ile Phe Asp Ser Gly Gly Cys
145                 150                 155                 160

Ala His Gln Phe Gly Glu Lys Gly Asp Ala Ala Gln Asp Ile Arg Tyr
                165                 170                 175

Pro Val Asp Val Thr Ile Thr Asn Asp Cys His Val Val Val Thr Asp
            180                 185                 190

Ala Gly Asp Arg Ser Ile Lys Val Phe Asp Phe Phe Gly Gln Ile Lys
        195                 200                 205

Leu Val Ile Gly Gly Gln Phe Ser Leu Pro Trp Gly Val Glu Thr Thr
210                 215                 220

Pro Gln Asn Gly Ile Val Val Thr Asp Ala Glu Ala Gly Ser Leu His
225                 230                 235                 240

Leu Leu Asp Val Asp Phe Ala Glu Gly Val Leu Arg Arg Thr Glu Arg
                245                 250                 255

Leu Gln Ala His Leu Cys Asn Pro Arg Gly Val Ala Val Ser Trp Leu
            260                 265                 270

Thr Gly Ala Ile Ala Val Leu Glu His Pro Leu Ala Leu Gly Thr Gly
        275                 280                 285

Val Cys Ser Thr Arg Val Lys Val Phe Ser Ser Met Gln Leu Val
290                 295                 300

Gly Gln Val Asp Thr Phe Gly Leu Ser Leu Tyr Phe Pro Ser Lys Ile
305                 310                 315                 320

Thr Ala Ser Ala Val Thr Phe Asp His Gln Gly Asn Val Ile Val Ala
                325                 330                 335

Asp Thr Ser Gly Pro Ala Ile Leu Cys Leu Gly Lys Pro Glu Phe
            340                 345                 350

Pro Val Pro Lys Pro Met Val Thr His Gly Leu Ser His Pro Val Ala
        355                 360                 365

Leu Thr Phe Thr Lys Glu Asn Ser Leu Leu Val Leu Asp Thr Ala Ser
370                 375                 380

His Ser Ile Lys Val Tyr Lys Val Asp Trp Gly
385                 390                 395
```

<210> SEQ ID NO 3

<211> LENGTH: 3008
<212> TYPE: DNA
<213> ORGANISM: Canis sp.
<220> FEATURE:
<221> NAME/KEY: CDS
<222> LOCATION: (698)..(1897)
<223> OTHER INFORMATION:
<220> FEATURE:
<221> NAME/KEY: misc_feature
<222> LOCATION: (2692)..(2692)
<223> OTHER INFORMATION: N=any nucleic acid
<220> FEATURE:
<221> NAME/KEY: misc_feature
<222> LOCATION: (2748)..(2748)
<223> OTHER INFORMATION: N=any nucleic acid
<220> FEATURE:
<221> NAME/KEY: misc_feature
<222> LOCATION: (2750)..(2750)
<223> OTHER INFORMATION: N=any nucleic acid
<220> FEATURE:
<221> NAME/KEY: misc_feature
<222> LOCATION: (2793)..(2793)
<223> OTHER INFORMATION: N=any nucleic acid
<220> FEATURE:
<221> NAME/KEY: misc_feature
<222> LOCATION: (2845)..(2845)
<223> OTHER INFORMATION: N=any nucleic acid
<220> FEATURE:
<221> NAME/KEY: misc_feature
<222> LOCATION: (2916)..(2916)
<223> OTHER INFORMATION: N=any nucleic acid
<220> FEATURE:
<221> NAME/KEY: misc_feature
<222> LOCATION: (2918)..(2918)
<223> OTHER INFORMATION: N=any nucleic acid
<220> FEATURE:
<221> NAME/KEY: misc_feature
<222> LOCATION: (2931)..(2931)
<223> OTHER INFORMATION: N=any nucleic acid
<220> FEATURE:
<221> NAME/KEY: misc_feature
<222> LOCATION: (2941)..(2941)
<223> OTHER INFORMATION: N=any nucleic acid
<220> FEATURE:
<221> NAME/KEY: misc_feature
<222> LOCATION: (2990)..(2990)
<223> OTHER INFORMATION: N=any nucleic acid

<400> SEQUENCE: 3

```
ccccaaggcc cccccggccc ccaggcaacc ccaggccccc aggcaaccca aggcccccg      60 gccccaagcc ccccaggttc ccggccccaa gaaccaagcc ccccggcccc ccgccccag     120 cacccagcac caagcccccg cccccccgccc caagcaccca gccccagcac ccagccccg    180 ccccagcccc agccccagca cccagccccc gcccagcac ccagcccag cacccagccc      240 ccgccccagc cccagccccc gtcccccccc ccagcaccca gccccagccc cagcagcagc    300
acccagcagg ggactgcaaa gcgtaggcta ccccaggtgg aacaccgtgt tctagttttg    360
ctttgccgtt tgcagcctgg gcgatcgggg gccaccgctc gagcctgttt cccgtcgcgg    420
aaagcggagc cgccccgccc cgcccccgc ctgcctgaag gtcacgggcc tgggcctgcg     480
gcgcgcggtg cggcccgcga gcgtccgctc ccgcgccctc gcagtcagc gcccgcccgc     540 ccgccggggg accgcaggcc gcggccgaga ggctgcgcgc tgcgcccgcg acgtcaggcc    600
ccgccccgcc ccgccccgcc ccgtgaccgg ccccggcccc ggccccggcc ccggccccgg    660
accgagcggc gcccgcggga gcggcggcgg ccgcgcg atg ggg gcc gaa gcg gcg     715
                                          Met Gly Ala Glu Ala Ala
                                            1               5 ggg agc ggg cgg gcg ctg cgg gag ctg gtg cgc gag gcc gag gtc agc      763
Gly Ser Gly Arg Ala Leu Arg Glu Leu Val Arg Glu Ala Glu Val Ser
         10                  15                  20
```

| | |
|---|---|
| ttg ctc gag tgc aag gtg tgc ttc gag agg ttc ggc cac cgc cag cag<br>Leu Leu Glu Cys Lys Val Cys Phe Glu Arg Phe Gly His Arg Gln Gln<br>       25                         30                         35 | 811 |
| cgc cgc ccg cgc aac ctg ccc tgc ggc cac gtg gtg tgc ctg gcc tgc<br>Arg Arg Pro Arg Asn Leu Pro Cys Gly His Val Val Cys Leu Ala Cys<br> 40                           45                        50 | 859 |
| gtg gcg gcc ctg gcg cac ccg cgg acg ctg gcc ctg gag tgc ccc ttc<br>Val Ala Ala Leu Ala His Pro Arg Thr Leu Ala Leu Glu Cys Pro Phe<br>55                        60                        65                        70 | 907 |
| tgc cgc cgg gcc tgc cgc ggc tgc gac acc agc gac tgc ctg ccg gtg<br>Cys Arg Arg Ala Cys Arg Gly Cys Asp Thr Ser Asp Cys Leu Pro Val<br>                   75                        80                        85 | 955 |
| ctt cac ctc ctg gag ctc ctg ggc tcg gcg ctg cgc cca gcc ccc gcc<br>Leu His Leu Leu Glu Leu Leu Gly Ser Ala Leu Arg Pro Ala Pro Ala<br>         90                         95                        100 | 1003 |
| gcc ccc cgc gcc gcc ccc cgc gcc gcc ccc tgc gcc ccg ggc gcc ctc<br>Ala Pro Arg Ala Ala Pro Arg Ala Ala Pro Cys Ala Pro Gly Ala Leu<br>         105                     110                     115 | 1051 |
| gcc tgc cat cac gcg ttc gga ggc tgg ggg acc ctg gtc aac ccc acg<br>Ala Cys His His Ala Phe Gly Gly Trp Gly Thr Leu Val Asn Pro Thr<br>120                        125                     130 | 1099 |
| ggg ctg gcg ctg tgc ccc aag acc ggg cgg gtc gtg gtg cac gac<br>Gly Leu Ala Leu Cys Pro Lys Thr Gly Arg Val Val Val His Asp<br>135                        140                     145                     150 | 1147 |
| ggc agg agg cgg gtc aag atc ttt gac tcc ggg gga gga tgc gcc cat<br>Gly Arg Arg Arg Val Lys Ile Phe Asp Ser Gly Gly Gly Cys Ala His<br>                   155                     160                     165 | 1195 |
| cag ttt gga gag aag ggg gag gct gcc cag gac att agg tac ccc ctg<br>Gln Phe Gly Glu Lys Gly Glu Ala Ala Gln Asp Ile Arg Tyr Pro Leu<br>         170                     175                     180 | 1243 |
| gac gtc gcc gtc acc aac gac tgc cac gtg gtt gtc acc gac gcc ggc<br>Asp Val Ala Val Thr Asn Asp Cys His Val Val Val Thr Asp Ala Gly<br>                 185                     190                     195 | 1291 |
| gac cgc tcc atc aaa gtg ttt gat ttc ttt ggc cag atc aag ctc gtc<br>Asp Arg Ser Ile Lys Val Phe Asp Phe Phe Gly Gln Ile Lys Leu Val<br>200                        205                     210 | 1339 |
| att gga gac cag ttt tcc tta cct tgg ggc gtg gag acc acc cct cag<br>Ile Gly Asp Gln Phe Ser Leu Pro Trp Gly Val Glu Thr Thr Pro Gln<br>215                        220                     225                     230 | 1387 |
| aat ggg gtc gtg gta act gac gcc gag gca ggg tcg ctg cac ctg ctg<br>Asn Gly Val Val Val Thr Asp Ala Glu Ala Gly Ser Leu His Leu Leu<br>                 235                     240                     245 | 1435 |
| gaa gtc gac ttt gca gaa gga gcc ctc cag agg act gaa aag ctg caa<br>Glu Val Asp Phe Ala Glu Gly Ala Leu Gln Arg Thr Glu Lys Leu Gln<br>         250                     255                     260 | 1483 |
| ggt cat ctg tgc aac ccg cga ggg gtg gcc gtg tcc tgg ctc act ggg<br>Gly His Leu Cys Asn Pro Arg Gly Val Ala Val Ser Trp Leu Thr Gly<br>                 265                     270                     275 | 1531 |
| gcc att gcg gtc ctg gag cac cct ccg ggg ctg ggg gct ggg gcg ggc<br>Ala Ile Ala Val Leu Glu His Pro Pro Gly Leu Gly Ala Gly Ala Gly<br>280                        285                     290 | 1579 |
| agc acc gcc gtg aag gtg ttc agc cca act atg cag ctg atc ggc cag<br>Ser Thr Ala Val Lys Val Phe Ser Pro Thr Met Gln Leu Ile Gly Gln<br>295                        300                     305                     310 | 1627 |
| gtg gat acc ttt ggg ctc agc ctc ttt ttc ccc tct aga ata acc gcc<br>Val Asp Thr Phe Gly Leu Ser Leu Phe Phe Pro Ser Arg Ile Thr Ala<br>                 315                     320                     325 | 1675 |
| tcc gcc gtg acc ttt gat cac cag ggg aat gtg att gtt gca gat act<br>Ser Ala Val Thr Phe Asp His Gln Gly Asn Val Ile Val Ala Asp Thr | 1723 |

-continued

|  |  |  |  |  |  |  |  |  |  |  |  |  |  |  |  |
|---|---|---|---|---|---|---|---|---|---|---|---|---|---|---|---|
|  |  |  | 330 |  |  |  | 335 |  |  |  | 340 |  |  |  |  |
| tct | agt | cag | gcc | gtc | cta | tgc | ttg | gga | cag | cct | gag | gaa | ttt | cca | gtc |
| Ser | Ser | Gln | Ala | Val | Leu | Cys | Leu | Gly | Gln | Pro | Glu | Glu | Phe | Pro | Val |
|  |  | 345 |  |  |  |  | 350 |  |  |  |  | 355 |  |  |  |

1771

| ctg | aag | ccc | atc | atc | acc | cat | ggt | ctt | tcc | cat | cct | gtg | gca | ctg | acc |
|---|---|---|---|---|---|---|---|---|---|---|---|---|---|---|---|
| Leu | Lys | Pro | Ile | Ile | Thr | His | Gly | Leu | Ser | His | Pro | Val | Ala | Leu | Thr |
| 360 |  |  |  |  | 365 |  |  |  |  | 370 |  |  |  |  |  |

1819

| ttc | acc | aag | gag | aat | tct | ctt | ctt | gtg | ctg | gac | agt | gca | gcc | cat | tcc |
|---|---|---|---|---|---|---|---|---|---|---|---|---|---|---|---|
| Phe | Thr | Lys | Glu | Asn | Ser | Leu | Leu | Val | Leu | Asp | Ser | Ala | Ala | His | Ser |
| 375 |  |  |  |  | 380 |  |  |  |  | 385 |  |  |  |  | 390 |

1867

| gta | aaa | gtc | tac | aag | gct | gac | tgg | ggg | taa | tggggtgtgg | tgggggtcct |
|---|---|---|---|---|---|---|---|---|---|---|---|
| Val | Lys | Val | Tyr | Lys | Ala | Asp | Trp | Gly |  |  |  |
|  |  |  |  | 395 |  |  |  |  |  |  |  |

1917

| ggaactgcca | ctaatccagt | ttaaccctgg | atgaattaat | cccatctctc | gaacggggat | 1977 |
|---|---|---|---|---|---|---|
| cattataact | gcctgacaga | cttataaagg | ttgaaggtaa | ttattaaaga | ataataatga | 2037 |
| agtctaccgt | ttattgagtt | atgtgctccc | tgtgctagga | aactttgcaa | atattagctc | 2097 |
| agcgtgtcct | tacagtggta | cccagggagg | taatgcccat | cattaatccc | attttagaga | 2157 |
| tgagaaaact | gagacccgag | ggtttaagtg | attctctgaa | ggtcatgttt | acttactgtg | 2217 |
| acagtcacaa | tgggaactct | attctgactc | cccaatccct | tgctcctaag | taggataaca | 2277 |
| gatgtgagaa | aacgacagca | tgtgtctata | tgttgttact | gtgtgtactc | tctttacagg | 2337 |
| tagctatttc | tcttggttgg | acgtgcagag | aaaggagact | ttctagagag | ttcaagagga | 2397 |
| aaaagggtag | tgtgatgagc | atggacgtga | gtgtcattga | acttgctggt | tctttgatgt | 2457 |
| cacagtaggt | agaatgactg | tggatccttc | aactgcccct | gggaaggta | aacatgtctg | 2517 |
| ttgggacctg | gatgtcctcc | atcataggaa | cccaggaaat | actagttggt | tgctgcagaa | 2577 |
| aggcttgtgt | ggacataagt | tcaaaactac | tgccgaccac | cgtacattca | cacacctcca | 2637 |
| gtgggagatg | gctggaagac | agtcctgtga | caggtctgca | ttcatagaac | aagangccgc | 2697 |
| caccgttggt | tcacggcaga | atgagtttgc | ctgcctcttc | ataatctgtg | ncnacccgaa | 2757 |
| acccttttgt | gatagagttt | ttctctgtgc | catttnaatt | tgtcccattg | cacacactgt | 2817 |
| tttccctaa | ccagctccct | tgatgctnag | ctagcattta | ggccactggt | aaaccctgt | 2877 |
| atacttcttg | agttgaagtt | aagctttgac | ccagataang | nctgctttaa | tacntgcagt | 2937 |
| cgantggacc | gaataagggg | gaaatttcag | gtgaggtggc | cgggttcttt | atnaaccggt | 2997 |
| tttggtttgt | a |  |  |  |  | 3008 |

<210> SEQ ID NO 4
<211> LENGTH: 399
<212> TYPE: PRT
<213> ORGANISM: Canis sp.
<220> FEATURE:
<221> NAME/KEY: misc_feature
<222> LOCATION: (2692)..(2692)
<223> OTHER INFORMATION: N=any nucleic acid
<220> FEATURE:
<221> NAME/KEY: misc_feature
<222> LOCATION: (2748)..(2748)
<223> OTHER INFORMATION: N=any nucleic acid
<220> FEATURE:
<221> NAME/KEY: misc_feature
<222> LOCATION: (2750)..(2750)
<223> OTHER INFORMATION: N=any nucleic acid
<220> FEATURE:
<221> NAME/KEY: misc_feature
<222> LOCATION: (2793)..(2793)
<223> OTHER INFORMATION: N=any nucleic acid
<220> FEATURE:
<221> NAME/KEY: misc_feature

```
<222> LOCATION: (2845)..(2845)
<223> OTHER INFORMATION: N=any nucleic acid
<220> FEATURE:
<221> NAME/KEY: misc_feature
<222> LOCATION: (2916)..(2916)
<223> OTHER INFORMATION: N=any nucleic acid
<220> FEATURE:
<221> NAME/KEY: misc_feature
<222> LOCATION: (2918)..(2918)
<223> OTHER INFORMATION: N=any nucleic acid
<220> FEATURE:
<221> NAME/KEY: misc_feature
<222> LOCATION: (2931)..(2931)
<223> OTHER INFORMATION: N=any nucleic acid
<220> FEATURE:
<221> NAME/KEY: misc_feature
<222> LOCATION: (2941)..(2941)
<223> OTHER INFORMATION: N=any nucleic acid
<220> FEATURE:
<221> NAME/KEY: misc_feature
<222> LOCATION: (2990)..(2990)
<223> OTHER INFORMATION: N=any nucleic acid

<400> SEQUENCE: 4

Met Gly Ala Glu Ala Ala Gly Ser Gly Arg Ala Leu Arg Glu Leu Val
  1               5                  10                  15

Arg Glu Ala Glu Val Ser Leu Leu Glu Cys Lys Val Cys Phe Glu Arg
                 20                  25                  30

Phe Gly His Arg Gln Gln Arg Arg Pro Arg Asn Leu Pro Cys Gly His
             35                  40                  45

Val Val Cys Leu Ala Cys Val Ala Ala Leu Ala His Pro Arg Thr Leu
 50                  55                  60

Ala Leu Glu Cys Pro Phe Cys Arg Arg Ala Cys Arg Gly Cys Asp Thr
 65                  70                  75                  80

Ser Asp Cys Leu Pro Val Leu His Leu Leu Glu Leu Leu Gly Ser Ala
                 85                  90                  95

Leu Arg Pro Ala Pro Ala Ala Pro Arg Ala Ala Pro Arg Ala Ala Pro
            100                 105                 110

Cys Ala Pro Gly Ala Leu Ala Cys His His Ala Phe Gly Gly Trp Gly
            115                 120                 125

Thr Leu Val Asn Pro Thr Gly Leu Ala Leu Cys Pro Lys Thr Gly Arg
130                 135                 140

Val Val Val Val His Asp Gly Arg Arg Val Lys Ile Phe Asp Ser
145                 150                 155                 160

Gly Gly Gly Cys Ala His Gln Phe Gly Glu Lys Gly Glu Ala Ala Gln
                165                 170                 175

Asp Ile Arg Tyr Pro Leu Asp Val Ala Val Thr Asn Asp Cys His Val
            180                 185                 190

Val Val Thr Asp Ala Gly Asp Arg Ser Ile Lys Val Phe Asp Phe Phe
            195                 200                 205

Gly Gln Ile Lys Leu Val Ile Gly Asp Gln Phe Ser Leu Pro Trp Gly
            210                 215                 220

Val Glu Thr Thr Pro Gln Asn Gly Val Val Thr Asp Ala Glu Ala
225                 230                 235                 240

Gly Ser Leu His Leu Leu Glu Val Asp Phe Ala Glu Gly Ala Leu Gln
                245                 250                 255

Arg Thr Glu Lys Leu Gln Gly His Leu Cys Asn Pro Arg Gly Val Ala
            260                 265                 270

Val Ser Trp Leu Thr Gly Ala Ile Ala Val Leu Glu His Pro Pro Gly
            275                 280                 285
```

```
Leu Gly Ala Gly Ala Gly Ser Thr Ala Val Lys Val Phe Ser Pro Thr
    290                 295                 300

Met Gln Leu Ile Gly Gln Val Asp Thr Phe Gly Leu Ser Leu Phe Phe
305                 310                 315                 320

Pro Ser Arg Ile Thr Ala Ser Ala Val Thr Phe Asp His Gln Gly Asn
                325                 330                 335

Val Ile Val Ala Asp Thr Ser Ser Gln Ala Val Leu Cys Leu Gly Gln
                340                 345                 350

Pro Glu Glu Phe Pro Val Leu Lys Pro Ile Ile Thr His Gly Leu Ser
            355                 360                 365

His Pro Val Ala Leu Thr Phe Thr Lys Glu Asn Ser Leu Leu Val Leu
    370                 375                 380

Asp Ser Ala Ala His Ser Val Lys Val Tyr Lys Ala Asp Trp Gly
385                 390                 395

<210> SEQ ID NO 5
<211> LENGTH: 12
<212> TYPE: DNA
<213> ORGANISM: Canis sp.

<400> SEQUENCE: 5 gccgccccc gc                                                            12

<210> SEQ ID NO 6
<211> LENGTH: 54
<212> TYPE: DNA
<213> ORGANISM: canis familiaris

<400> SEQUENCE: 6
ctgcgcccag ccccgccgc ccccgcgcc gccccgcg ccgccccctg cgcc               54

<210> SEQ ID NO 7
<211> LENGTH: 42
<212> TYPE: DNA
<213> ORGANISM: Mus musculus

<400> SEQUENCE: 7
ctccacgcgt ccccggctgc cctcagcgcc gccccttcg cg                          42

<210> SEQ ID NO 8
<211> LENGTH: 42
<212> TYPE: DNA
<213> ORGANISM: Rattus norvegicus

<400> SEQUENCE: 8
ctccacgcgt ccccggctgc cctcagcgcc gcctcctgtg cg                         42

<210> SEQ ID NO 9
<211> LENGTH: 42
<212> TYPE: DNA
<213> ORGANISM: Sus scrofa

<400> SEQUENCE: 9
cttcgcccgg cgcccgcggc ctcccgcggc gccccctcct cc                         42

<210> SEQ ID NO 10
<211> LENGTH: 42
<212> TYPE: DNA
<213> ORGANISM: Homo Sapiens

<400> SEQUENCE: 10
```

-continued cttcgccagt ccccggccgc ccatcgcgcc gcccccagcg cc               42

<210> SEQ ID NO 11
<211> LENGTH: 42
<212> TYPE: DNA
<213> ORGANISM: Pan troglodytes

<400> SEQUENCE: 11
cttcgccagt ccccggccgc ccaccgcgcc gcccccagcg cc               42

<210> SEQ ID NO 12
<211> LENGTH: 34
<212> TYPE: DNA
<213> ORGANISM: Felis catus

<400> SEQUENCE: 12
agcccccgcc gcccaccgcg ccgcccccag cgcc                        34

<210> SEQ ID NO 13
<211> LENGTH: 34
<212> TYPE: DNA
<213> ORGANISM: Panthera leo

<400> SEQUENCE: 13
agcccccgcc gcccaccgcg ccgcccccag cgcc                        34

<210> SEQ ID NO 14
<211> LENGTH: 34
<212> TYPE: DNA
<213> ORGANISM: Panthera tigris

<400> SEQUENCE: 14
agcccccgcc gcccaccgcg ccgcccccag cgcc                        34

<210> SEQ ID NO 15
<211> LENGTH: 34
<212> TYPE: DNA
<213> ORGANISM: Panthera pardus

<400> SEQUENCE: 15
agcccccgcc gcccaccgcg ccgcccccag cgcc                        34

<210> SEQ ID NO 16
<211> LENGTH: 34
<212> TYPE: DNA
<213> ORGANISM: Panthera unicia

<400> SEQUENCE: 16
agcccccgcc gcccaccgcg ccgcccccag cgcc                        34

<210> SEQ ID NO 17
<211> LENGTH: 34
<212> TYPE: DNA
<213> ORGANISM: Acinonyx jubatus

<400> SEQUENCE: 17
agcccccgcc gcccaccgcg ccgcccccag cgcc                        34

<210> SEQ ID NO 18
<211> LENGTH: 34
<212> TYPE: DNA
<213> ORGANISM: Lynx caracal

<400> SEQUENCE: 18

```
agccccgcc gcccaccgcg ccgccccag cgcc                            34

<210> SEQ ID NO 19
<211> LENGTH: 46
<212> TYPE: DNA
<213> ORGANISM: Canis familiaris

<400> SEQUENCE: 19 agccccgcc gccccgcg ccgccccg cgccgccccc tgcgcc                  46

<210> SEQ ID NO 20
<211> LENGTH: 34
<212> TYPE: DNA
<213> ORGANISM: Canis familiaris

<400> SEQUENCE: 20 agccccgcc gccccgcg ccgcccctg cgcc                              34

<210> SEQ ID NO 21
<211> LENGTH: 46
<212> TYPE: DNA
<213> ORGANISM: Canis lupus

<400> SEQUENCE: 21 agccccgcc gccccgcg ccgccccg cgccgccccc tgcgcc                  46

<210> SEQ ID NO 22
<211> LENGTH: 34
<212> TYPE: DNA
<213> ORGANISM: Canis lupus

<400> SEQUENCE: 22 agccccgcc gccccgcg ccgcccctg cgcc                              34

<210> SEQ ID NO 23
<211> LENGTH: 46
<212> TYPE: DNA
<213> ORGANISM: Canis lupus

<400> SEQUENCE: 23 agccccgcc gccccgcg ccgccccg cgccgccccc tgcgcc                  46

<210> SEQ ID NO 24
<211> LENGTH: 34
<212> TYPE: DNA
<213> ORGANISM: Canis lupus

<400> SEQUENCE: 24 agccccgcc gccccgcg ccgcccctg cgcc                              34

<210> SEQ ID NO 25
<211> LENGTH: 46
<212> TYPE: DNA
<213> ORGANISM: Canis rufus

<400> SEQUENCE: 25 agccccgcc gccccgcg ccgccccg cgccgccccc tgcgcc                  46

<210> SEQ ID NO 26
<211> LENGTH: 34
<212> TYPE: DNA
<213> ORGANISM: Canis rufus
```

<400> SEQUENCE: 26 agccccgcc gccccgcg ccgcccctg cgcc                34

<210> SEQ ID NO 27
<211> LENGTH: 46
<212> TYPE: DNA
<213> ORGANISM: Canis latrans

<400> SEQUENCE: 27 agccccgcc gccccgcg ccgccccg cgcgccccc tgcgcc       46

<210> SEQ ID NO 28
<211> LENGTH: 34
<212> TYPE: DNA
<213> ORGANISM: Canis latrans

<400> SEQUENCE: 28 agccccgcc gccccgcg ccgcccctg cgcc                34

<210> SEQ ID NO 29
<211> LENGTH: 46
<212> TYPE: DNA
<213> ORGANISM: Canis aureus

<400> SEQUENCE: 29 agccccgcc gccccgcg ccgccccg cgcgccccc tgcgcc       46

<210> SEQ ID NO 30
<211> LENGTH: 34
<212> TYPE: DNA
<213> ORGANISM: Canis aureus

<400> SEQUENCE: 30 agccccgcc gccccgcg ccgcccctg cgcc                34

<210> SEQ ID NO 31
<211> LENGTH: 46
<212> TYPE: DNA
<213> ORGANISM: Cuon alpinus

<400> SEQUENCE: 31 agccccgcc gccccgcg ccgccccg cgcgccccc tgcgcc       46

<210> SEQ ID NO 32
<211> LENGTH: 46
<212> TYPE: DNA
<213> ORGANISM: Dusicyon griseus

<400> SEQUENCE: 32 agccccgcc gccccgcg ccgccccg cgcgccccc tgcgcc       46

<210> SEQ ID NO 33
<211> LENGTH: 34
<212> TYPE: DNA
<213> ORGANISM: Dusicyon griseus

<400> SEQUENCE: 33 agccccgcc gccccgcg ccgcccctg cgcc                34

<210> SEQ ID NO 34
<211> LENGTH: 34
<212> TYPE: DNA
<213> ORGANISM: Urocyon littoralis

<400> SEQUENCE: 34 agccccgcc gcccccgcg ccgcccctg cgcc                    34

<210> SEQ ID NO 35
<211> LENGTH: 34
<212> TYPE: DNA
<213> ORGANISM: Conepatus semistriatus

<400> SEQUENCE: 35
aggccccgcc gcccccgcg ccgcccctg cgcc                   34

<210> SEQ ID NO 36
<211> LENGTH: 34
<212> TYPE: DNA
<213> ORGANISM: Ursus americanus

<400> SEQUENCE: 36 agccccgcc gcccccgcg ccgcccctg cagc                    34

<210> SEQ ID NO 37
<211> LENGTH: 34
<212> TYPE: DNA
<213> ORGANISM: Ursus americanus

<400> SEQUENCE: 37
aggccccgcc gcccccgcg ccgctccctg cgcc                  34

<210> SEQ ID NO 38
<211> LENGTH: 34
<212> TYPE: DNA
<213> ORGANISM: Ursus maritimus

<400> SEQUENCE: 38 agccccgcc gcccccgcg ccgcccctg cagc                    34

<210> SEQ ID NO 39
<211> LENGTH: 34
<212> TYPE: DNA
<213> ORGANISM: Ursus arctos

<400> SEQUENCE: 39
aggccccgcc gcccccgcg ccgcccctg cagc                   34

<210> SEQ ID NO 40
<211> LENGTH: 34
<212> TYPE: DNA
<213> ORGANISM: Ursus arctos

<400> SEQUENCE: 40 agccccgcc gcccccgcg ccgcccctg cagc                    34

<210> SEQ ID NO 41
<211> LENGTH: 31
<212> TYPE: DNA
<213> ORGANISM: Ursus horribilis

<400> SEQUENCE: 41 ccccgcgcc cccgcgccg ccccctgcag c                      31

<210> SEQ ID NO 42
<211> LENGTH: 34
<212> TYPE: DNA

```
<213> ORGANISM: Procyonidae lotor

<400> SEQUENCE: 42
aggccccgcc gcccccgcg ccgctccctg cgcc                              34

<210> SEQ ID NO 43
<211> LENGTH: 34
<212> TYPE: DNA
<213> ORGANISM: Potos flavus

<400> SEQUENCE: 43
aggccccgcc gcccccgcg ccgcccctg cacc                               34

<210> SEQ ID NO 44
<211> LENGTH: 34
<212> TYPE: DNA
<213> ORGANISM: Bessaricyon beddari

<400> SEQUENCE: 44
aggccccgcc gcccccgcg ccgctccctg cgcc                              34

<210> SEQ ID NO 45
<211> LENGTH: 34
<212> TYPE: DNA
<213> ORGANISM: Nasua nasua

<400> SEQUENCE: 45
aggccccgcc gcccccgcg ccgcgccctg cgcc                              34

<210> SEQ ID NO 46
<211> LENGTH: 34
<212> TYPE: DNA
<213> ORGANISM: Gulo gulo

<400> SEQUENCE: 46
aggccccgcc gcccccgcg ccgcgccctg cgcc                              34

<210> SEQ ID NO 47
<211> LENGTH: 34
<212> TYPE: DNA
<213> ORGANISM: Galictis vittata

<400> SEQUENCE: 47
aggccccgcc gcccccgcg ccgcgccctg cgcc                              34

<210> SEQ ID NO 48
<211> LENGTH: 34
<212> TYPE: DNA
<213> ORGANISM: Mustela vison

<400> SEQUENCE: 48
aggccccgcc gcccccgcg ccgcgccctg cgcc                              34

<210> SEQ ID NO 49
<211> LENGTH: 34
<212> TYPE: DNA
<213> ORGANISM: Martes pennanti

<400> SEQUENCE: 49
agtccccgcc gcccccgcg ccgtgccctg cgcc                              34

<210> SEQ ID NO 50
<211> LENGTH: 34
```

```
<212> TYPE: DNA
<213> ORGANISM: Lutra canadiens

<400> SEQUENCE: 50
aggccccgcc gccccccgcg ccgcgccgtg cgcc                              34

<210> SEQ ID NO 51
<211> LENGTH: 28
<212> TYPE: DNA
<213> ORGANISM: L. maculicollis

<400> SEQUENCE: 51
cgccgccccc cgcgccgcgc cctgcgcc                                     28

<210> SEQ ID NO 52
<211> LENGTH: 34
<212> TYPE: DNA
<213> ORGANISM: Melogale moschata

<400> SEQUENCE: 52
aggccccgcc gccccccgcg ccgcgccgtg cgcc                              34

<210> SEQ ID NO 53
<211> LENGTH: 19
<212> TYPE: DNA
<213> ORGANISM: Artificial Sequence
<220> FEATURE:
<223> OTHER INFORMATION: An artificially synthesized primer sequence

<400> SEQUENCE: 53
actgtgaccg tgaccgaga                                               19

<210> SEQ ID NO 54
<211> LENGTH: 20
<212> TYPE: DNA
<213> ORGANISM: Artificial Sequence
<220> FEATURE:
<223> OTHER INFORMATION: An artificially synthesized primer sequence

<400> SEQUENCE: 54
cacaccccaa ggtaaggaga                                              20

<210> SEQ ID NO 55
<211> LENGTH: 20
<212> TYPE: DNA
<213> ORGANISM: Artificial Sequence
<220> FEATURE:
<223> OTHER INFORMATION: An artificially synthesized primer sequence

<400> SEQUENCE: 55
gactgccatg tggttgtcac                                              20

<210> SEQ ID NO 56
<211> LENGTH: 22
<212> TYPE: DNA
<213> ORGANISM: Artificial Sequence
<220> FEATURE:
<223> OTHER INFORMATION: An artificially synthesized primer sequence

<400> SEQUENCE: 56
aaacaattca ttaatggcag ca                                           22

<210> SEQ ID NO 57
<211> LENGTH: 20
<212> TYPE: DNA
```

```
-continued

<213> ORGANISM: Artificial Sequence
<220> FEATURE:
<223> OTHER INFORMATION: An artificially synthesized primer sequence

<400> SEQUENCE: 57
gtcaccatca ccaacgactg                                                    20

<210> SEQ ID NO 58
<211> LENGTH: 20
<212> TYPE: DNA
<213> ORGANISM: Artificial Sequence
<220> FEATURE:
<223> OTHER INFORMATION: An artificially synthesized primer sequence

<400> SEQUENCE: 58
tgcgaaagac catgagtgac                                                    20

<210> SEQ ID NO 59
<211> LENGTH: 20
<212> TYPE: DNA
<213> ORGANISM: Artificial Sequence
<220> FEATURE:
<223> OTHER INFORMATION: An artificially synthesized primer sequence

<400> SEQUENCE: 59
ggatccatgg cggccgaagc                                                    20

<210> SEQ ID NO 60
<211> LENGTH: 28
<212> TYPE: DNA
<213> ORGANISM: Artificial Sequence
<220> FEATURE:
<223> OTHER INFORMATION: An artificially synthesized primer sequence

<400> SEQUENCE: 60
gcggccgcac aattcattaa tggcagac                                           28
```